United States Patent [19]
Getman et al.

[11] Patent Number: 6,087,359
[45] Date of Patent: Jul. 11, 2000

[54] THIOARYL SULFONAMIDE HYDROXAMIC ACID COMPOUNDS

[76] Inventors: Daniel P. Getman, 66 Sunny Hill Ct., Chesterfield, Mo. 63017; Daniel P. Becker, 1800 Mapelwood La., Glenview, Ill. 60025; Thomas E. Barta, 1133 Maple Ave. #3W, Evanston, Ill. 60202; Clara I. Villamil, 813 Long Rd., Glenview, Ill. 60025; Susan L. Hockerman, 5319 W. Hutchingson, Chicago, Ill. 60641; Louis J. Bedell, 1832 E. Campl McDonald Rd., Mt. Prospect, Ill. 60056; Hui Li, 322 Jefferson Ct., Vernon Hills, Ill. 60061; John N. Freskos, 7572 York, Clayton, Mo. 63105; Robert M. Heintz, 603 Nancy Pl.; Joseph J. McDonald, 1036 Johanna Dr., both of Ballwin, Mo. 63021; Gary A. DeCrescenzo, 7345 Spruce Hill Ct., St. Charles, Mo. 63304

[21] Appl. No.: 09/254,534
[22] PCT Filed: Mar. 4, 1998
[86] PCT No.: PCT/US98/04298
 § 371 Date: Sep. 10, 1999
 § 102(e) Date: Sep. 10, 1999
[87] PCT Pub. No.: WO98/39313
 PCT Pub. Date: Sep. 11, 1998

Related U.S. Application Data

[60] Provisional application No. 60/039,795, Mar. 4, 1997.
[51] Int. Cl.[7] ................ A61K 31/5375; A61K 31/5377; C07D 295/15; C07D 413/12
[52] U.S. Cl. ................ 514/238.2; 544/116; 544/120; 544/122; 544/127; 544/128; 544/131; 544/132; 544/133; 544/134; 544/137; 544/138; 544/139; 544/141; 544/143; 544/144; 544/145; 544/146; 544/148; 544/149; 544/153; 544/159; 546/234
[58] Field of Search ................ 544/159, 141; 514/238.2

[56] References Cited

U.S. PATENT DOCUMENTS 5,646,167  7/1997  MacPherson et al. .

FOREIGN PATENT DOCUMENTS 0 757 984 A1  2/1997  European Pat. Off. .
WO 93/14069  7/1993  WIPO .
WO 97/20824  6/1997  WIPO .

*Primary Examiner*—Robert W. Ramsuer
*Attorney, Agent, or Firm*—Welsh & Katz, Ltd.

[57] ABSTRACT

A thioaryl sulfonamide hydroxamic acid compound that inter alia inhibits matrix metalloprotease activity is disclosed as are a treatment process that comprises administering a contemplated thioaryl sulfonamide hydroxamic acid compound in a MMP enzyme-inhibiting effective amount to a host having a condition associated with pathological matrix metalloprotease activity.

19 Claims, No Drawings

THIOARYL SULFONAMIDE HYDROXAMIC ACID COMPOUNDS

This application is a 371 of PCT/US98/04298 filed Mar. 4, 1998 which claims the benefit of Provisional application 60/039,795 filed Mar. 4, 1997.

TECHNICAL FIELD

This invention is directed to proteinase (protease) inhibitors, and more particularly to thioaryl sulfonamide hydroxamic acid compounds that are useful, inter alia, as inhibitors for matrix metalloproteinases, compositions of those compounds, intermediates for the syntheses of the compounds, processes for the preparation of the compounds and processes for treating pathological conditions associated with pathological matrix metalloproteinase activity.

BACKGROUND OF THE INVENTION

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals makeup, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason leads to a number of disease states. Inhibition of the enzymes responsible loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function are the zinc metalloproteinases (metalloproteases, or MMPs).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; corneal, epidermal or gastric ulceration; tumor metastasis, invasion or angiogenesis; periodontal disease; proteinuria; Alzheimer's Disease; coronary thrombosis and bone disease. Defective injury repair processes also occur. This can produce improper wound healing leading to weak repairs, adhesions and scarring. These latter defects can lead to disfigurement and/or permanent disabilities as with post-surgical adhesions.

Matrix metalloproteases are also involved in the biosynthesis of tumor necrosis factor (TNF) and inhibition of the production or action of TNF and related compounds is an important clinical disease treatment mechanism. TNF-$\alpha$, for example, is a cytokine that at present is thought to be produced initially as a 28 kD cell-associated molecule. It is released as an active, 17 kD form that can mediate a large number of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal.

TNF-$\alpha$ convertase is a metalloproteinase involved in the formation of active TNF-$\alpha$. Inhibition of TNF-$\alpha$ convertase inhibits production of active TNF-$\alpha$. Compounds that inhibit both MMPs activity have been disclosed in WIPO International Publication Nos. WO 94/24140, WO 94/02466 and WO 97/20824. There remains a need for effective MMP and TNF-$\alpha$ convertase inhibiting agents. Compounds that inhibit MMPs such as collagenase, stromelysin and gelatinase have been shown to inhibit the release of TNF (Gearing et al. Nature 376, 555-557 (1994), McGeehan et al., Nature 376, 558–561 (1994)).

MMPs are involved in other biochemical processes in mammals as well. Included is the control of ovulation, post-partum uterine involution, possibly implantation, cleavage of APP ($\beta$-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin (MMP-3), gelatinase (MMP-2), gelatinase B (MMP-9) or collagenase III (MMP-13) are the relatively most important enzyme or enzymes to inhibit especially when compared with collagenase I (MMP-1). A drug that does not inhibit collagenase I can have a superior therapeutic profile. Osteoarthritis, another prevalent disease wherein it is believed that cartilage degradation in inflamed joints is at least partially caused by MMP-13 released from cells such as stimulated chrondrocytes, may be best treated by administration of drugs one of whose modes of action is inhibition of MMP-13. See, for example, Mitchell et al., J. Clin. Invest., 97:761–768 (1996) and Reboul et al., J. Clin. Invest., 97:2011–2019 (1996).

Inhibitors of metalloproteases are known. Examples include natural biochemicals such as tissue inhibitor of metalloproteinase (TIMP), $\alpha_2$-macroglobulin and their analogs or derivatives. These are high molecular weight protein molecules that form inactive complexes with metalloproteases. A number of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure.

Thiol group-containing amide or peptidyl amide-based metalloprotease (MMP) inhibitors are known as is shown in, for example, WO95/12389, WO96/11209 and U.S. Pat. No. 4,595,700. Hydroxamate group-containing MMP inhibitors are disclosed in a number of published patent applications such as WO 95/29892, WO 97/24117, WO 97/49679 and EP 0 780 386 that disclose carbon back-boned compounds, and WO 90/05719, WO 93/20047, WO 95/09841 and WO 96/06074 that disclose hydroxamates that have a peptidyl back-bones or peptidomimetic back-bones, as does the article by Schwartz et al., Progr. Med. Chem., 29:271–334 (1992) and those of Rasmussen et al., Pharmacol. Ther., 75(1): 69–75 (1997) and Denis et al., Invest. New Drugs, 15(3): 175–185 (1997).

One possible problem associated with known MMP inhibitors is that such compounds often exhibit the same or similar inhibitory effects against each of the MMP enzymes. For example, the peptidomimetic hydroxamate known as batimastat is reported to exhibit $IC_{50}$ values of about 1 to about 20 nanomolar (nM) against each of MMP-1, MMP-2, MMP-3, MMP-7, and MMP-9. Marimastat, another peptidomimetic hydroxamate was reported to be another broad-spectrum MMP inhibitor with an enzyme inhibitory spectrum very similar to batimastat, except that marimastat exhibited an $IC_{50}$ value against MMP-3 of 230 nM. Rasmussen et al., Pharmacol. Ther., 75(1): 69–75 (1997).

Meta analysis of data from Phase I/II studies using marimastat in patients with advanced, rapidly progressive, treatment-refractory solid tumor cancers (colorectal, pancreatic, ovarian, prostate) indicated a dose-related reduction in the rise of cancer-specific antigens used as surrogate markers for biological activity. Although marimastat exhibited some measure of efficacy via these markers, toxic side effects were noted. The most common drug-related toxicity of marimastat in those clinical trials was musculoskeletal pain and stiffness, often commencing in the small joints in the hands, spreading to the arms and shoulder. A short dosing holiday of 1–3 weeks followed by dosage reduction permits treatment to continue. Rasmussen et al., Pharmacol. Ther., 75(1): 69–75 (1997). It is thought that the lack of specificity of inhibitory effect among the MMPs may be the cause of that effect.

In view of the importance of hydroxamate MMP inhibitor compounds in the treatment of several diseases and the lack of enzyme specificity exhibited by two of the more potent drugs now in clinical trials, it would be a great benefit if hydroxamates of greater enzyme specificity could be found. This would be particularly the case if the hydroxamate inhibitors exhibited strong inhibitory activity against one or more of MMP-2, MMP-9 or MMP-13 that are associated with several pathological conditions, while at the same time exhibiting limited inhibition of MMP-1, an enzyme that is relatively ubiquitous and as yet not associated with any pathological condition. The disclosure that follows describes one family of hydroxamate MMP inhibitors that exhibit those desirable activities.

BRIEF SUMMARY OF THE INVENTION

The present invention is directed to a family of molecules that inter alia inhibit matrix metalloprotease (MMP) activity, and particularly inhibit the activity of one or more of MMP-2, MMP-9, or MMP-13, while generally exhibiting little activity against MMP-1, as well as a process for treating a mammal having a condition associated with pathological activity.

Briefly, one embodiment of the present invention is directed to a thioaryl sulfonamide hydroxamic acid compound. That compound corresponds in structure to Formula I

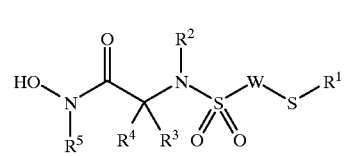

wherein:
W is arylene or heteroarylene;
$R^1$ is selected from the group consisting of a heterocyclo, cycloalkyl, heterocycloalkyl, aralkyl, heteroaralkyl, hydroxycarbonylalkyl, aralkoxyalkyl, aryloxyalkyl, hydroxyalkyl, alkanoylalkyl, aralkanoylalkyl, arylcarbonylalkyl, haloalkyl, aralkylaryl, aryloxyalkylaryl, aralkoxyaryl, alkylthioalkyl, alkylthioaryl, arylthioalkyl, alkylthioaralkyl, aralkylthioalkyl, aralkylthioaryl substituent, the sulfoxide or sulfone of any of said thio substituents, an aryl, heteroaryl, and a fused ring structure substituent comprising two or more 5 or 6 membered rings selected from the group consisting of aryl, heteroaryl, carbocyclic and heterocyclic. The aryl, cycloalkyl and heteroaryl substituents of which $R^1$ can be comprised is optionally substituted (unsubstituted or substituted) with one or more substituents independently selected from the group consisting of a halo, alkyl, alkoxy, nitro, cyano, perfluoroalkyl, trifluoromethylalkyl, hydroxy, thiol, hydroxycarbonyl, aryloxy, arylthio, arylamino, aralkyl, aryl, heteroaryloxy, heteroarylthio, heteroarylamino, heteroaralkyl, cycloalkyl, alkoxycarbonylalkyl, heterocyclooxy, hydroxycarbonylalkyl, heterocyclothio, heterocycloamino, cycloalkyloxy, cycloalkylthio, cycloalkylamino, heteroaralkoxy, heteroaralkylthio, heteroaralkylamino, aralkoxy, aralkylthio, aralkylamino, heterocyclic, heteroaryl, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, hydroxycarbonylalkoxy, alkoxycarbonylalkyl, alkylhydroxycarbonylalkylthio, alkoxycarbonylalkoxy, alkoxycarbonylalkylthio, amino, alkanylcarbonylamino, arylcarbonylamino, cycloalkylcarbonylamino, heterocycloalkylcarbonylamino, aralkylcarbonylamino, heteroarylcarbonylamino, heteroaralkanylcarbonylamino, heterocycloalkyloxy, alkylsulfonylamino, arylsulfonylamino, aralkylsulfonylamino, heteroarylsulfonylamino, heteroaralkylsulfonylamino, cycloalkylsulfonylamino, heterocycloalkylsulfonylamino and N-monosubstituted or N,N-disubstituted aminoalkyl group wherein the substituent(s) on the nitrogen are selected from the group consisting of alkyl, aryl, aralkyl, cycloalkyl, aralkoxycarbonyl, alkoxycarbonyl, and alkanoyl, or wherein the nitrogen and two substituents attached thereto form a 5 to 8 member heterocyclo or heteroaryl ring.

$R^2$ is independently selected from the group consisting of a hydrogen (hydrido), alkyl, aryl, aralkyl, heteroaryl, heteroaralkyl, alkynyl, alkenyl, thiolalkyl, cycloalkyl, cycloalkylalkyl, heterocycloalkyl, alkoxyalkyl, aralkoxyalkyl, aminoalkyl, alkoxyalkoxyalkyl, aryloxyalkyl, hydroxyalkyl, hydroxycarbonylalkyl, hydroxycarbonylaralkyl, aminocarbonylalkyl, and N-monosubstituted or N,N-disubstituted aminocarbonylalkyl group wherein the substituent(s) on the nitrogen are selected from the group consisting of alkyl, aryl, aralkyl, cycloalkyl and alkanoyl, or wherein the nitrogen and two substituents attached thereto form a 5- to 8-membered heterocyclo or heteroaryl ring. Aryl or heteroaryl groups or substituents can be optionally substituted (unsubstituted or substituted) with one or more substituents independently selected from the group consisting of a halo, alkyl, alkoxy, nitro, cyano, perfluoroalkyl, trifluoromethylalkyl, hydroxy, thiol, hydroxycarbonyl, aryloxy, arylthio, arylamino, aralkyl, aryl, heteroaryloxy, heteroarylthio, heteroarylamino, heteroaralkyl, cycloalkyl, heterocyclooxy, heterocyclothio, heterocycloamino, cycloalkyloxy, cycloalkylthio, cycloalkylamino, heteroaralkoxy, heteroaralkylthio, heteroaralkylamino, aralkoxy, aralkylthio, aralkylamino, heterocyclic, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, alkanylcarbonylamino, arylcarbonylamino, cycloalkylcarbonylamino, heterocycloalkylcarbonylamino, aralkylcarbonylamino, heteroarylcarbonylamino, heteroaralkanylcarbonylamino, alkylsulfonylamino, arylsulfonylamino, aralkylsulfonylamino, heteroarylsulfonylamino, heteroaralkylsulfonylamino, cycloalkylsulfonylamino, heterocycloalkylsulfonylamino and N-monosubstituted or N,N-disubstituted aminoalkyl group wherein the substituent(s) on the nitrogen are selected from the group consisting of alkyl, aryl, aralkyl, cycloalkyl, aralkoxycarbonyl, alkoxycarbonyl, and alkanoyl, or wherein the nitrogen and two substituents attached thereto form a 5- to 8-membered heterocyclo or heteroaryl ring;

$R^3$ and $R^4$ and are independently selected from the group consisting of a hydrogen (hydrido), alkyl, cycloalkyl, cycloalkylalkyl, alkoxyalkyl, hydroxyalkyl, aryloxyalkyl, aralkoxyalkyl, aralkyl, aryl, heteroaryl, heteroaralkyl, heterocyclo, heterocycloalkyl, hydroxycarbonylalkyl, alkoxycarbonylalkyl, aralkoxycarbonylalkyl, hydroxycarbonyl, alkoxycarbonyl, perfluoroalkyl, trifluoromethyl, trifluoromethylalkyl, thiolalkyl, alkylthioalkyl, arylthioalkyl, aralkylthioalkyl, heteroaralkylthioalkyl, or a sulfoxide or sulfone of any of said thio substituents, aminocarbonyl, aminocarbonylalkyl and N-monosubstituted or N,N-disubstituted aminocarbonyl or aminocarbonylalkyl group wherein the substituent(s) on the nitrogen are independently selected from among alkyl, aryl, aralkyl, heteroaralkyl, cycloalkyl and alkanoyl, or wherein the nitrogen and two substituents attached thereto form a 5- to 8-membered heterocyclo or heteroaryl ring, or $R^2$ and $R^3$ or $R^2$ and $R^4$, independently, together with the atoms to which they are attached optionally form a 3- to 8-membered ring or $R^3$ and $R^4$ together with the atom to which they are attached form a 3- to 8-membered ring.

Particularly preferred inhibitor compounds have a structure that corresponds to Formula III, below,

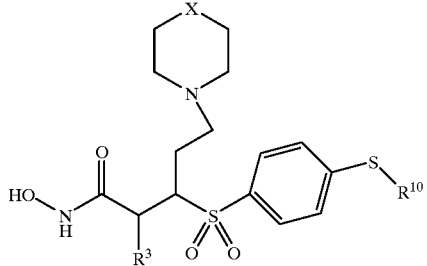

III wherein $R^3$ is as before defined, $R^4$ is hydrido and is not shown, $R^{10}$ is a six-membered aryl, cycloalkyl or heteroaryl ring and X is O or $CH_2$.

Among the several benefits and advantages of the present invention are the provision of compounds and compositions effective as inhibitors of matrix metalloproteinase activity, and the provision of such compounds and compositions that are effective for the inhibition of metalloproteinases implicated in diseases and disorders involving uncontrolled breakdown of connective tissue.

More particularly, a benefit of this invention is the provision of a compound and composition effective for inhibiting metalloproteinases, particularly MMP-13 and/or MMP-2, associated with pathological conditions such as, for example, rheumatoid arthritis, osteoarthritis, septic arthritis, corneal, epidermal or gastric ulceration, tumor metastasis, invasion or angiogenesis, periodontal disease, proteinuria, Alzheimer's Disease, coronary thrombosis and bone disease.

An advantage of the invention is the provision of a method for preparing such compositions. Another benefit is the provision of a method for treating a pathological condition associated with abnormal matrix metalloproteinase activity.

Another advantage of the invention is the provision of compounds, compositions and methods effective for treating such pathological conditions by selective inhibition of a metalloproteinase such as MMP-13 and MMP-2 associated with such conditions with minimal side effects resulting from inhibition of other proteinases such as MMP-1, whose activity is necessary or desirable for normal body function.

Still further benefits and advantages of the invention will be apparent to the skilled worker from the disclosure that follows.

DETAILED DESCRIPTION OF THE INVENTION

In accordance with the present invention, it has been found that certain thioaryl sulfonamide hydroxamic acid compounds, are effective, inter alia, for inhibition of matrix metalloproteinases ("MMPs") believed to be associated with uncontrolled or otherwise pathological breakdown of connective tissue. In particular, it has been found that these certain thioaryl sulfonyl compounds are effective for inhibition of collagenase III (MMP-13) and also gelatinase A (MMP-2), which can be particularly destructive to tissue if present or generated in abnormal quantities or concentrations, and thus exhibit a pathological activity.

Moreover, it has been discovered that many of these thioaryl sulfonyl compounds are selective in the inhibition of MMPs associated with diseased conditions without excessive inhibition of other collagenases essential to normal bodily function such as tissue turnover and repair. More particularly, it has been found that particularly preferred thioaryl sulfonyl compounds are particularly active in inhibiting of MMP-13 and/or MMP-2, while having a limited or minimal effect on MMP-1. This point is discussed in detail hereinafter and is illustrated in the Inhibition Table hereinafter. The subject compounds are characterized as substituted-aryl or heteroaryl sulfonamide, sulfinamide or sulfenamide carboxylic acids or hydroxamic acids.

Contemplated compounds correspond in structure to Formula I:

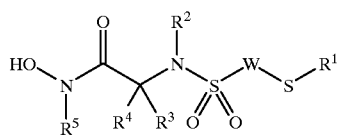

I wherein:
W is arylene or heteroarylene:
R$^1$ is selected from the group consisting of a heterocyclo, cycloalkyl, heterocycloalkyl, aralkyl, heteroaralkyl, hydroxycarbonylalkyl, aralkoxyalkyl, aryloxyalkyl, hydroxyalkyl, alkanoylalkyl, aralkanoylalkyl, arylcarbonylalkyl, haloalkyl, aralkylaryl, aryloxyalkylaryl, aralkoxyaryl, alkylthioalkyl, alkylthioaryl, arylthioalkyl, alkylthioaralkyl, aralkylthioalkyl, aralkylthioaryl substituent, the sulfoxide or sulfone of any of said thio substituents, an aryl, heteroaryl, and a fused ring structure substituent comprising two or more 5 or 6 membered rings selected from the group consisting of aryl, heteroaryl, carbocyclic and heterocyclic.

The aryl, cycloalkyl and heteroaryl substituents of which R$^1$ can be comprised is optionally substituted (unsubstituted or substituted) with one or more substituents independently selected from the group consisting of a halo, alkyl, alkoxy, nitro, cyano, perfluoroalkyl, trifluoromethylalkyl, hydroxy, thiol, hydroxycarbonyl, aryloxy, arylthio, arylamino, aralkyl, aryl, heteroaryloxy, heteroarylthio, heteroarylamino, heteroaralkyl, cycloalkyl, alkoxycarbonylalkyl, heterocyclooxy, hydroxycarbonylalkyl, heterocyclothio, heterocycloamino, cycloalkyloxy, cycloalkylthio, cycloalkylamino, heteroaralkoxy, heteroaralkylthio, heteroaralkylamino, aralkoxy, aralkylthio, aralkylamino, heterocyclic, heteroaryl, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, hydroxycarbonylalkoxy, alkoxycarbonylalkyl, alkylhydroxycarbonylalkylthio, alkoxycarbonylalkoxy, alkoxycarbonylalkylthio, amino, alkanylcarbonylamino, arylcarbonylamino, cycloalkylcarbonylamino, heterocycloalkylcarbonylamino, aralkylcarbonylamino, heteroarylcarbonylamino, heteroaralkanylcarbonylamino, heterocycloalkyloxy, alkylsulfonylamino, arylsulfonylamino, aralkylsulfonylamino, heteroarylsulfonylamino, heteroaralkylsulfonylamino, cycloalkylsulfonylamino, heterocycloalkylsulfonylamino and N-monosubstituted or N,N-disubstituted aminoalkyl group wherein the substituent(s) on the nitrogen are selected from the group consisting of alkyl, aryl, aralkyl, cycloalkyl, aralkoxycarbonyl, alkoxycarbonyl, and alkanoyl, or wherein the nitrogen and two substituents attached thereto form a 5 to 8 member heterocyclo or heteroaryl ring.

R$^2$ is independently selected from the group consisting of a hydrogen (hydrido), alkyl, aryl, aralkyl, heteroaryl, heteroaralkyl, alkynyl, alkenyl, thiolalkyl, cycloalkyl, cycloalkylalkyl, heterocycloalkyl, alkoxyalkyl, aralkoxyalkyl, aminoalkyl, alkoxyalkoxyalkyl, aryloxyalkyl, hydroxyalkyl, hydroxycarbonylalkyl, hydroxycarbonylaralkyl, aminocarbonylalkyl, and N-monosubstituted or N,N-disubstituted aminocarbonylalkyl group wherein the substituent(s) on the nitrogen are selected from the group consisting of alkyl, aryl, aralkyl, cycloalkyl and alkanoyl, or wherein the nitrogen and two substituents attached thereto form a 5- to 8-membered heterocyclo or heteroaryl ring.

Aryl or heteroaryl groups or substituents can be optionally substituted (unsubstituted or substituted) with one or more substituents independently selected from the group consisting of a halo, alkyl, alkoxy, nitro, cyano, perfluoroalkyl, trifluoromethylalkyl, hydroxy, thiol, hydroxycarbonyl, aryloxy, arylthio, arylamino, aralkyl, aryl, heteroaryloxy, heteroarylthio, heteroarylamino, heteroaralkyl, cycloalkyl, heterocyclooxy, heterocyclothio, heterocycloamino, cycloalkyloxy, cycloalkylthio, cycloalkylamino, heteroaralkoxy, heteroaralkylthio, heteroaralkylamino, aralkoxy, aralkylthio, aralkylamino, heterocyclic, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, alkanylcarbonylamino, arylcarbonylamino, cycloalkylcarbonylamino, heterocycloalkylcarbonylamino, aralkylcarbonylamino, heteroarylcarbonylamino, heteroaralkanylcarbonylamino, alkylsulfonylamino, arylsulfonylamino, aralkylsulfonylamino, heteroarylsulfonylamino, heteroaralkylsulfonylamino, cycloalkylsulfonylamino, heterocycloalkylsulfonylamino and N-monosubstituted or N,N-disubstituted aminoalkyl group wherein the substituent(s) on the nitrogen are selected from the group consisting of alkyl, aryl, aralkyl, cycloalkyl, aralkoxycarbonyl, alkoxycarbonyl, and alkanoyl, or wherein the nitrogen and two substituents attached thereto form a 5- to 8-membered heterocyclo or heteroaryl ring.

R$^3$ and R$^4$ and are independently selected from the group consisting of a hydrogen (hydrido), alkyl, cycloalkyl, cycloalkylalkyl, alkoxyalkyl, hydroxyalkyl, aryloxyalkyl, aralkoxyalkyl, aralkyl, aryl, heteroaryl, heteroaralkyl, heterocyclo, heterocycloalkyl, hydroxycarbonylalkyl, alkoxycarbonylalkyl, aralkoxycarbonylalkyl, hydroxycarbonyl, alkoxycarbonyl, perfluoroalkyl, trifluoromethyl, trifluoromethylalkyl, thiolalkyl, alkylthioalkyl, arylthioalkyl, aralkylthioalkyl, heteroaralkylthioalkyl, or a sulfoxide or sulfone of any of said thio substituents, aminocarbonyl, aminocarbonylalkyl and N-monosubstituted or N,N-disubstituted aminocarbonyl or aminocarbonylalkyl group wherein the substituent(s) on the nitrogen are independently selected from among alkyl, aryl, aralkyl, heteroaralkyl, cycloalkyl and alkanoyl, or wherein the nitrogen and two substituents attached thereto form a 5- to 8-membered heterocyclo or heteroaryl ring, or $R^2$ and $R^3$ or $R^2$ and $R^4$, independently, together with the atoms to which they are attached optionally form a 3-to 8-membered ring or $R^3$ and $R^4$ together with the atom to which they are attached form a 3-to 8-membered ring.

The present invention further relates to compounds of Formula II:

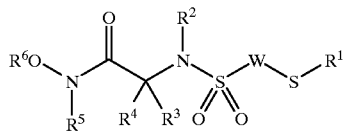

wherein:

W, $R^1$, $R^2$, $R^3$, and $R^4$ are as defined for Formula I; and $R^6$ represents a hydrido, $C_1$–$C_6$ alkyl, aryl, substituted aryl, arylalkyl or substituted arylalkyl radical. In preferred practice, W is a monocyclic aryl or heteroaryl group and $R^1$ is an aryl or heteroaryl radical.

Particularly preferred W groups are single-ringed (monocyclic) arylene or heteroarylene groups (divalent aromatic radicals) that are preferably substituted at positions corresponding to the 1- and 4-positions when phenylene. Those groups include 1,4-phenylene and the pyridylene radicals (2,5-pyridylene and 3,6-pyridylene). Particularly preferred $R^1$ groups include cyclohexyl, cyclopentyl (cycloalkyl), phenyl (aryl), each of the three pyridyl (2-, 3- and 4-) groups, as well as pyrimidyl, imidazolyl, thiazolyl, oxazolyl, and pyrazinyl (heteroaryl) groups, with aryl and heteroaryl groups being more preferred. Phenylene is a most preferred W group, whereas phenyl is a most preferred $R^1$ radical so that the substituent —W—S—$R^1$ is most preferably thiophenopxyphenyl.

Particularly preferred $R^2$ substituents are cylcoalkylalkyl and hererocycloalkylalkyl,with herterocycloalkylalkyl being most preferred. Of those particularly and most preferred substituents, the substituted alkyl group is preferably an ethyl (ethylene) group, the ring structure preferably contains six atoms, and heteroatoms when present are preferably at the 1- or 4-positions, or both.

Particularly preferred inhibitor compounds have a structure that corresponds to Formula III, below

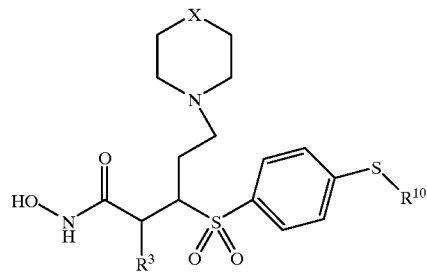

wherein $R^2$ is as before defined, $R^4$ is hydrido and is not shown, $R^{10}$ is a six-membered aryl, cycloalkyl or heteroaryl ring and X is O or $CH_2$.

A most preferred compound thus corresponds in structure to Formula IIIA, below, wherein the substituents are as defined before.

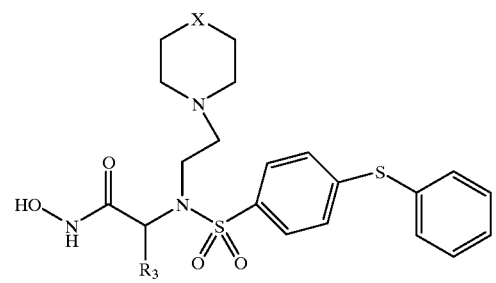

More preferred contemplated compounds have the stereochemistry depicted in Formula IV, below, wherein substituents are as defined before.

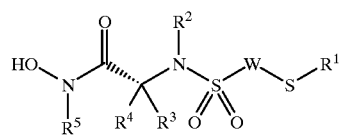

Most preferred inhibitor compounds therefore have the stereochemistry depicted in Formula V, below, wherein substituents are as defined before, and $R^{10}$ is aryl or heteroaryl.

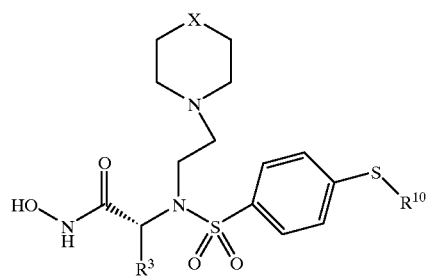

In more preferred practice, $R^{10}$ is aryl or heteroaryl, $R^2$ is cycloalkylalkyl or heterocycloalkylalkyl, $R^4$ is hydrido and $R^3$ is alkyl.

As utilized herein, the term "alkyl", alone or in combination, means a straight-chain or branched-chain alkyl radical containing from 1 to about 12, preferably from 1 to about 10, carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radial having one or more double bonds and containing from 2 to about 12 carbon atoms preferably from 2 to about 10 carbon atoms. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. The term "alkynyl", alone or in combination, means a straight-chain hydrocarbon radical having one or more triple bonds and containing from, 2 to about 12 carbon atoms preferably from 2 to about 10 carbon atoms. Examples of alkynyl radicals include ethynyl, 2-propynyl, 3-propynyl, decynyl, 1-butynyl, 2-butynyl, 3-butynyl, and the like.

The term "carbonyl", alone or in combination, means a —C(=O)— group wherein the remaining two bonds (valences) can be independently substituted. The term "thiol" or "sulfhydryl", alone or in combination, means a —SH group. The term "thio" or "thia", alone or in combination, means a thiaether group, i.e., a ether group wherein the ether oxygen is replaced by a sulfur atom.

The term "amino", alone or in combination, means an amine or —NH$_2$ group whereas the term mono-substituted amino, alone or in combination, means a substituted amine —N(H)(substituent) group wherein one hydrogen atom is replaced with a substituent and disubstituted amine means a —N(substituent)$_2$ wherein two hydrogen atoms for the amino group are replaced with independently selected substituent groups. Amines, amino groups and amides are classes that can be designated as primary (I°), secondary (II°) or tertiary (III°) or unsubstituted, mono-substituted or di-substituted depending on the degree of substitution of the amino nitrogen. Quaternary amine (IV°) means a nitrogen with four substituents (—N$^+$(substituent)$_4$) that is positively charged and accompanied by a counter ion or N-oxide means one substituent is oxygen and the group is represented as (—N$^+$(substituent)$_3$—O$^-$), i.e., the charges are internally compensated.

The term "cyano", alone or in combination, means a —C-triple bond-N (—CN)group. The term "azido", alone or in combination, means a —N-double bond—N-double bond-N (—N=N=N) group.

The term "hydroxyl", alone or in combination, means a —OH group. The term "nitro", alone or in combination, means a —NO$_2$ group.

The term "azo", alone or in combination, means a —N=N— group wherein the bonds at the terminal positions can be independently substituted. The term "hydrazino", alone or in combination, means a —NH—NH— group wherein the remaining two bonds (valences) can be independently substituted. The hydrogen atoms of the hydrazino group can be replaced, independently, with substituents and the nitrogen atoms can form acid addition salts or be quaternized.

The term "sulfonyl", alone or in combination, means a —S(O)$_2$— group wherein the remaining two bonds (valences) can be independently substituted. The term "sulfoxido", alone or in combination, means a —S(O)$_1$— group wherein the remaining two bonds (valences) can be independently substituted.

The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means an alkyl radical which contains from about 3 to about 8 carbon atoms and is cyclic. The term "cycloalkylalkyl" means an alkyl radical as defined above which is substituted by a cycloalkyl radical containing from about 3 to about 8, preferably from about 3 to about 6, carbon atoms. Examples of such cycloalkyl radicals include cyclopropyl, cyclobutyl, cyclopentyl, cyclohexyl and the like.

The term "aryl", alone or in combination, means a phenyl, or naphthyl radical which optionally carries one or more substituents selected from alkyl, alkoxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. The term "aralkoxycarbonyl", alone or in combination, means a radical of the formula —C(O)—O-aralkyl in which the term "aralkyl" has the significance given above. An example of an aralkoxycarbonyl radical is benzyloxycarbonyl. The term "aryloxy" means a radical of the formula aryl-O— in which the term aryl has the significance given above.

The terms "alkanoyl" or "alkylcarbonyl", alone or in combination, means an acyl radical derived from an alkanecarboxylic acid, examples of which include acetyl, propionyl, butyryl, valeryl, 4-methylvaleryl, and the like. The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl, 2-acetamido-1,2,3,4-tetrahydro-2-naphthoyl. The terms "aralkanoyl" or "aralkylcarbonyl" mean an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl and the like. The terms "aroyl" or "arylcarbonyl" mean an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The heterocyclyl (heterocyclo) or heterocycloalkyl portion of a heterocyclylcarbonyl, heterocyclyloxycarbonyl, heterocyclylalkoxycarbonyl, or heterocyclyalkyl group or the like is a saturated or partially unsaturated monocyclic, bicyclic or tricyclic heterocycle which contains one or more hetero atoms selected from nitrogen, oxygen and sulphur, which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, aryl or arylalkyl or on a tertiary nitrogen atom (i.e. =N—) by oxido and which is attached via a carbon atom. The tertiary nitrogen atom with three substituents can also attached to form a N-oxide (=N(O)—) group.

The heteroaryl portion of a heteroaroyl, heteroaryloxycarbonyl, or a heteroaralkoxy carbonyl group or the like is an aromatic monocyclic, bicyclic, or tricyclic heterocycle which contains the hetero atoms and is optionally substituted as defined above with respect to the definition of heterocyclyl. Examples of such heterocyclyl and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, pyrazinyl, pyrimidinyl, furyl, tetrahydrofuryl, thienyl, triazolyl, oxazolyl, oxadiazoyl, thiazolyl, thiadiazoyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolinyl, etc.), 1,2,3,4-tetrahydroisoquinolinyl (e.g., 1,2,3,4-tetrahydro-1-oxo-isoquinolinyl, etc.), quinoxalinyl, β-carbolinyl, 2-benzofurancarbonyl, benzothiophenyl, 1-, 2-, 4- or 5-benzimidazolyl, and the like.

The term "cycloalkylalkoxycarbonyl" means an acyl group derived from a cycloalkylalkoxycarboxylic acid of the formula cycloalkylalkyl—O—COOH wherein cycloalkylalkyl has the significance given above. The term "aryloxyalkanoyl" means an acyl radical of the formula aryl-O-alkanoyl wherein aryl and alkanoyl have the significance given above. The term "heterocyclyloxycarbonyl" means an acyl group derived from heterocyclyl-O—COOH wherein heterocyclyl is as defined above. The term "heterocyclylalkanoyl" is an acyl radical derived from a heterocyclyl-substituted alkane carboxylic acid wherein heterocyclyl has the significance given above. The term "heterocyclylalkoxycarbonyl" means an acyl radical derived from a heterocyclyl-substituted alkane-O—COOH wherein heterocyclyl has the significance given above. The term "heteroaryloxycarbonyl" means an acyl radical derived from a carboxylic acid represented by heteroaryl-O—COOH wherein heteroaryl has the significance given above.

The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, and alkyl, aryl, aralkyl, cycloalkyl, cycloalkylalkyl radicals and the like. The term "aminoalkanoyl" means an acyl group derived from an amino-substituted alkanecarboxylic acid wherein the amino group can be a primary, secondary or tertiary amino group containing substituents independently selected from hydrogen, alkyl, aryl, aralkyl, cycloalkyl, cycloalkylalkyl radicals and the like.

The term "halogen" or "halo" means fluorine, chlorine, bromine or iodine. The term "haloalkyl" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like. The term perfluoroalkyl means an alkyl group wherein each hydrogen has been replaced by a fluorine atom. Examples of such perfluoroalkyl groups, in addition to trifluoromethyl above, are perfluorobutyl, perfluoroisopropyl, perfluorododecyl and perfluorodecyl. The term "aromatic ring" in combinations such as substituted-aromatic ring thioether, substituted-aromatic ring sulfoxide or substituted-aromatic ring sulfone means aryl or heteroaryl as defined above.

Set forth in Table 1 to Table 14 inclusive and in Example 1a to Example 8d inclusive are several series of preferred classes of compounds. The Tables specifically include and are based on generic Formula I, wherein W is 1,4-disubstituted phenyl; n is O; R', $R^2$, $R^3$, and $R^4$ are as shown in the respective Table and $R^5$ is hydrogen:

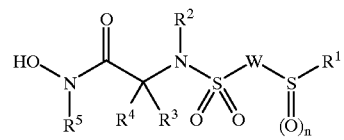

I

Expressly included among the individual compounds of the present invention are carboxylic acid compounds corresponding to each of the hydroxamic acid compounds of Tables 1 through 14. Each such carboxylic acid compound has the structure depicted for the corresponding hydroxamic acid compound of the tables, except that the carboxylic acid contains an HO— group in the same location in the structure as the HO—NH group of the hydroxamic acid. Thus, the invention specifically includes a carboxylic acid compound corresponding to each of the compounds of exemplary compounds (Examples) 1–9 of Table 1; compounds of Examples 1–13 of Table 2; the compounds of Examples 1–13 of Table 3; the compounds of Examples 1–12 of Table 4; the compounds of Examples 1–8 of Table 5; the compounds of Examples 1–9 of Table 6; the compounds of Examples 1–6 of Table 7; the compounds of Examples 1–5 of Table 8; the compounds of Examples 1–10 of Table 9; the compounds of Examples 1–9 of Table 10; the compounds of Examples 1–9 of Table 11; the compounds of Examples 1–9 of Table 12; the compounds of Examples 1–6 of Table 13; and the compounds of Examples 1–14 of Table 14. The invention specifically includes the carboxylic acid compounds corresponding to each of working Examples 1a "through" 8d as set out hereinbelow.

TABLE 1

| Example | R1 | R2 | R3 | R4 |
|---|---|---|---|---|
| 1 | S—⟨phenyl with CH₃, CH₃⟩ | 2-(N-morpholin-yl)ethyl | i-Pr | H |
| 2 | S—⟨phenyl with Cl⟩ | 2-(N-morpholin-yl)ethyl | i-Pr | H |
| 3 | S—⟨phenyl with OMe⟩ | 2-(N-morpholin-yl)ethyl | i-Pr | H |
| 4 | S—⟨phenyl with Cl⟩ | 2-(N-morpholin-yl)ethyl | i-Pr | H |
| 5 | S—⟨phenyl with OMe⟩ | 2-(N-morpholin-yl)ethyl | i-Pr | H |

TABLE 1-continued
| Example | R1 | R2 | R3 | R4 |
|---------|----|----|----|-----|
| 6 | 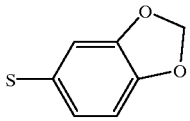 | 2-(N-morpholinyl)ethyl | i-Pr | H |
| 7 | 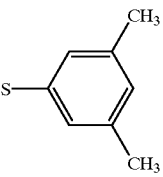 | 2-(N-morpholinyl)ethyl | i-Pr | H |
| 8 | 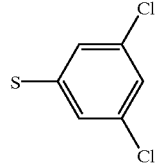 | 2-(N-morpholinyl)ethyl | i-Pr | H |
| 9 | 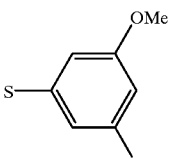 | 2-(N-morpholinyl)ethyl | i-Pr | H |
TABLE 2
| Example | R1 | R2 | R3 | R4 |
|---------|----|----|----|-----|
| 1 | 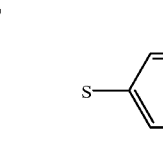 | 2-(N-morpholinyl)ethyl | i-Pr | H |
| 2 | 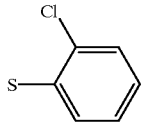 | 2-(N-morpholinyl)ethyl | i-Pr | H |
| 3 |  | 2-(N-morpholinyl)ethyl | i-Pr | H |
| 4 | 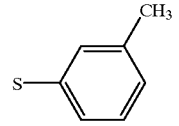 | 2-(N-morpholinyl)ethyl | i-Pr | H |
| 5 | 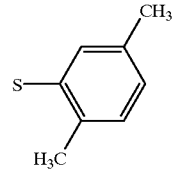 | 2-(N-morpholinyl)ethyl | i-Pr | H |
| 6 | 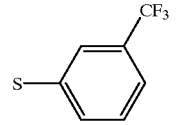 | 2-(N-morpholinyl)ethyl | i-Pr | H |
| 7 |  | 2-(N-morpholinyl)ethyl | i-Pr | H |

TABLE 2-continued

| Example | R1 | R2 | R3 | R4 |
|---------|----|----|----|----|
| 8 | 2,5-dimethoxyphenylthio | 2-(N-morpholinyl)ethyl | i-Pr | H |
| 9 | 3,4-dimethoxyphenylthio | 2-(N-morpholinyl)ethyl | i-Pr | H |
| 10 | 4-(2-carboxyethyl)phenylthio | 2-(N-morpholinyl)ethyl | i-Pr | H |
| 11 | 4-cyclohexylphenylthio | 2-(N-morpholinyl)ethyl | i-Pr | H |
| 12 | 4-(methylthio)phenylthio | 2-(N-morpholinyl)ethyl | i-Pr | H |
| 13 | 2-(N-methylcarbamoyl)phenylthio | 2-(N-morpholinyl)ethyl | i-Pr | H |

TABLE 3
| Example | R1 | R2 | R3 | R4 |
|---|---|---|---|---|
| 1 | 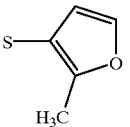 | 2-(N-morpholinyl)ethyl | i-Pr | H |
| 2 | 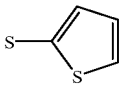 | 2-(N-morpholinyl)ethyl | i-Pr | H |
| 3 | 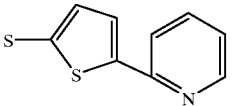 | 2-(N-morpholinyl)ethyl | i-Pr | H |
| 4 | 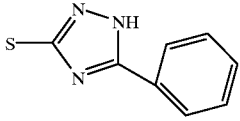 | 2-(N-morpholinyl)ethyl | i-Pr | H |
| 5 | 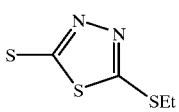 | 2-(N-morpholinyl)ethyl | i-Pr | H |
| 6 | 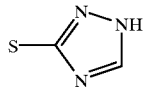 | 2-(N-morpholinyl)ethyl | i-Pr | H |
| 7 | 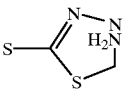 | 2-(N-morpholinyl)ethyl | i-Pr | H |
| 8 | 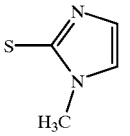 | 2-(N-morpholinyl)ethyl | i-Pr | H |
| 9 | 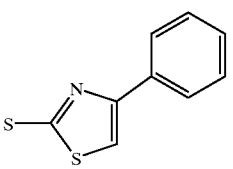 | 2-(N-morpholinyl)ethyl | i-Pr | H |
| 10 | 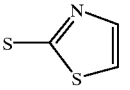 | 2-(N-morpholinyl)ethyl | i-Pr | H |
| 11 | 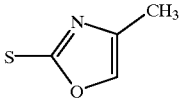 | 2-(N-morpholinyl)ethyl | i-Pr | H |

TABLE 3-continued

| Example | R1 | R2 | R3 | R4 |
|---|---|---|---|---|
| 12 | 5-mercapto-3-(pyridin-4-yl)-4H-1,2,4-triazole | 2-(N-morpholinyl)ethyl | i-Pr | H |
| 13 | 5-mercapto-2-(pyridin-4-yl)-1,3,4-oxadiazole | 2-(N-morpholinyl)ethyl | i-Pr | H |

TABLE 4

| Example | R1 | R2 | R3 | R4 |
|---|---|---|---|---|
| 1 | 5-mercapto-3-phenyl-1,2,4-thiadiazole | 2-(N-morpholinyl)ethyl | i-Pr | H |
| 2 | 5-mercapto-2-phenyl-1,3,4-oxadiazole | 2-(N-morpholinyl)ethyl | i-Pr | H |
| 3 | 5-mercapto-2-(pyridin-2-yl)-1,3,4-oxadiazole | 2-(N-morpholinyl)ethyl | i-Pr | H |
| 4 | 5-mercapto-2-(pyridin-3-yl)-1,3,4-oxadiazole | 2-(N-morpholinyl)ethyl | i-Pr | H |
| 5 | 5-mercapto-2-(thiophen-2-yl)-1,3,4-oxadiazole | 2-(N-morpholinyl)ethyl | i-Pr | H |
| 6 | 5-mercapto-3-tert-butyl-4H-1,2,4-triazole | 2-(N-morpholinyl)ethyl | i-Pr | H |
| 7 | 5-mercapto-3-(furan-2-yl)-4H-1,2,4-triazole | 2-(N-morpholinyl)ethyl | i-Pr | H |
| 8 | 5-mercapto-3-phenyl-1,2,4-oxadiazole | 2-(N-morpholinyl)ethyl | i-Pr | H |
| 9 | 5-mercapto-1-ethyl-1H-tetrazole | 2-(N-morpholinyl)ethyl | i-Pr | H |
| 10 | 5-mercapto-2-methyl-2H-tetrazole | 2-(N-morpholinyl)ethyl | i-Pr | H |
| 11 | 5-mercapto-1-benzyl-1H-tetrazole | 2-(N-morpholinyl)ethyl | i-Pr | H |
| 12 | 5-mercapto-1H-tetrazole | 2-(N-morpholinyl)ethyl | i-Pr | H |

TABLE 5

| Example | R1 | R2 | R3 | R4 |
|---|---|---|---|---|
| 1 | 2-mercaptobenzimidazole | 2-(N-morpholinyl)ethyl | i-Pr | H |
| 2 | 2-mercapto-5-methylbenzimidazole | 2-(N-morpholinyl)ethyl | i-Pr | H |
| 3 | 2-mercapto-6-methoxybenzimidazole | 2-(N-morpholinyl)ethyl | i-Pr | H |
| 4 | 2-mercaptobenzoxazole | 2-(N-morpholinyl)ethyl | i-Pr | H |
| 5 | 2-mercaptobenzothiazole | 2-(N-morpholinyl)ethyl | i-Pr | H |
| 6 | 2-mercaptothiazolo[5,4-b]pyridine | 2-(N-morpholinyl)ethyl | i-Pr | H |
| 7 | 2-mercaptoimidazo[4,5-c]pyridine | 2-(N-morpholinyl)ethyl | i-Pr | H |
| 8 | 2-mercaptothiazolo[4,5-b]pyridine | 2-(N-morpholinyl)ethyl | i-Pr | H |

TABLE 6

| Example | R1 | R2 | R3 | R4 |
|---|---|---|---|---|
| 1 | 2-mercapto-4-methylpyrimidine | 2-(N-morpholinylethyl) | i-Pr | H |
| 2 | 2-mercapto-5-(trifluoromethyl)pyridine | 2-(N-morpholinylethyl) | i-Pr | H |
| 3 | 2-mercaptopyridine | 2-(N-morpholinylethyl) | i-Pr | H |
| 4 | 4-mercaptopyridine | 2-(N-morpholinylethyl) | i-Pr | H |
| 5 | 4-mercapto-6-methoxypyrimidine | 2-(N-morpholinylethyl) | i-Pr | H |

TABLE 6-continued

| Example | R1 | R2 | R3 | R4 |
|---|---|---|---|---|
| 6 | 4,6-dichloropyrimidin-2-ylthio | 2-(N-morpholinylethyl) | i-Pr | H |
| 7 | quinolin-2-ylthio | 2-(N-morpholinylethyl) | i-Pr | H |
| 8 | quinolin-8-ylthio | 2-(N-morpholinylethyl) | i-Pr | H |
| 9 | quinazolin-4-ylthio | 2-(N-morpholinylethyl) | i-Pr | H |

TABLE 7

| Example | R1 | R2 | R3 | R4 |
|---|---|---|---|---|
| 1 | cyclopropylthio | 2-(N-morpholinyl)ethyl | i-Pr | H |
| 2 | cyclobutylthio | 2-(N-morpholinyl)ethyl | i-Pr | H |
| 3 | cyclopentylthio | 2-(N-morpholinyl)ethyl | i-Pr | H |
| 4 | cyclohexylthio | 2-(N-morpholinyl)ethyl | i-Pr | H |

TABLE 7-continued

| Example | R1 | R2 | R3 | R4 |
|---|---|---|---|---|
| 5 | cycloheptylthio | 2-(N-morpholinyl)ethyl | i-Pr | H |
| 6 | cyclooctylthio | 2-(N-morpholinyl)ethyl | i-Pr | H |

TABLE 8

| Example | R1 | R2 | R3 | R4 |
|---|---|---|---|---|
| 1 | cyclopropylmethylthio | 2-(N-morpholinyl)ethyl | i-Pr | H |
| 2 | cyclobutylmethylthio | 2-(N-morpholinyl)ethyl | i-Pr | H |
| 3 | cyclopentylmethylthio | 2-(N-morpholinyl)ethyl | i-Pr | H |
| 4 | cyclohexylmethylthio | 2-(N-morpholinyl)ethyl | i-Pr | H |
| 5 | cycloheptylmethylthio | 2-(N-morpholinyl)ethyl | i-Pr | H |

TABLE 9

| Example | R1 | R2 | R3 | R4 |
|---------|----|----|----|----|
| 1 | S-CH2-phenyl | 2-(N-morpholinyl)ethyl | i-Pr | H |
| 2 | S-CH2-(2-methylphenyl) | 2-(N-morpholinyl)ethyl | i-Pr | H |
| 3 | S-CH2-(3-methylphenyl) | 2-(N-morpholinyl)ethyl | i-Pr | H |
| 4 | S-CH2-(4-methoxyphenyl) | 2-(N-morpholinyl)ethyl | i-Pr | H |
| 5 | S-CH2-(4-carboxyphenyl) | 2-(N-morpholinyl)ethyl | i-Pr | H |
| 6 | S-CH2-(3,4-methylenedioxyphenyl) | 2-(N-morpholinyl)ethyl | i-Pr | H |
| 7 | S-CH2CH2-phenyl | 2-(N-morpholinyl)ethyl | i-Pr | H |
| 8 | S-CH2CH2-N(Et)-CH2-phenyl | 2-(N-morpholinyl)ethyl | i-Pr | H |
| 9 | S-CH2CH2CH2-phenyl | 2-(N-morpholinyl)ethyl | i-Pr | H |
| 10 | S-CH2-C(O)-NH-(4-methylphenyl) | 2-(N-morpholinyl)ethyl | i-Pr | H |

TABLE 10
| Example | R1 | R2 | R3 | R4 |
|---|---|---|---|---|
| 1 |  | 2-(N-morpholinyl)ethyl | i-Pr | H |
| 2 |  | 2-(N-morpholinyl)ethyl | i-Pr | H |
| 3 |  | 2-(N-morpholinyl)ethyl | i-Pr | H |
| 4 |  | 2-(N-morpholinyl)ethyl | i-Pr | H |
| 5 |  | 2-(N-morpholinyl)ethyl | i-Pr | H |
| 6 |  | 2-(N-morpholinyl)ethyl | i-Pr | H |
| 7 |  | 2-(N-morpholinyl)ethyl | i-Pr | H |
| 8 |  | 2-(N-morpholinyl)ethyl | i-Pr | H |
| 9 |  | 2-(N-morpholinyl)ethyl | i-Pr | H |
TABLE 11
| Example | R1 | R2 | R3 | R4 |
|---|---|---|---|---|
| 1 |  | 2-(N-morpholinyl)ethyl | i-Pr | H |
| 2 |  | 2-(N-morpholinyl)ethyl | i-Pr | H |
| 3 |  | 2-(N-morpholinyl)ethyl | i-Pr | H |

TABLE 11-continued

| Example | R1 | R2 | R3 | R4 |
|---|---|---|---|---|
| 4 | S-CH2-C(=O)-NHCH3 | 2-(N-morpholinyl)ethyl | i-Pr | H |
| 5 | S-Et | 2-(N-morpholinyl)ethyl | i-Pr | H |
| 6 | S-propyl | 2-(N-morpholinyl)ethyl | i-Pr | H |
| 7 | S-butyl | 2-(N-morpholinyl)ethyl | i-Pr | H |
| 8 | S-pentyl | 2-(N-morpholinyl)ethyl | i-Pr | H |
| 9 | S-hexyl | 2-(N-morpholinyl)ethyl | i-Pr | H |

TABLE 12

| Example | R1 | R2 | R3 | R4 |
|---|---|---|---|---|
| 1 | S-(p-tolyl) | propyl-pyrrolidin-1-yl | i-Pr | H |
| 2 | S-(p-tolyl) | propyl-piperidin-1-yl | i-Pr | H |
| 3 | S-(p-tolyl) | propyl-azepan-1-yl | i-Pr | H |
| 4 | S-(p-tolyl) | propyl-N(CH3)2 | i-Pr | H |
| 5 | S-(p-tolyl) | propyl-N(Et)2 | i-Pr | H |
| 6 | S-(p-tolyl) | propyl-N(i-Pr)2 | i-Pr | H |
| 7 | S-(p-tolyl) | ethyl-2-pyridyl | i-Pr | H |
| 8 | S-(p-tolyl) | ethyl-3-pyridyl | i-Pr | H |
| 9 | S-(p-tolyl) | ethyl-4-pyridyl | i-Pr | H |

TABLE 13

| Example | R1 | R2 | R3 | R4 |
|---------|----|----|----|----|
| 1 | S-C6H4-CH3 (p-tolylthio) | -CH2CH2-morpholine | i-Pr | H |
| 2 | S-C6H4-CH3 | -CH2CH2-morpholine | CH3 | H |
| 3 | S-C6H4-CH3 | -CH2CH2-morpholine | H | H |
| 4 | S-C6H4-CH3 | -CH2CH2-morpholine | CH3 | CH3 |
| 5 | S-C6H4-CH3 | -CH2CH2-morpholine | -CH2CH(CH3)2 (isobutyl) | H |
| 6 | S-C6H4-CH3 | -CH2CH2-morpholine | -CH(CH3)CH2CH3 (sec-butyl) | H |

35

TABLE 14

| Example | R1 | R2 | R3 | R4 |
|---------|----|----|----|----|
| 1 | S-C6H4-CH3 | -CH2CH2-morpholine | -CH2CH2-SH | H |
| 2 | S-C6H4-CH3 | -CH2CH2-morpholine | -CH2CH2CH2-SCH3 | H |
| 3 | S-C6H4-CH3 | -CH2CH2-morpholine | -CH2CH2-C6H5 | H |
| 4 | S-C6H4-CH3 | -CH2CH2-morpholine | -CH2CH2-C6H4-OH (p-hydroxyphenethyl) | H |

TABLE 14-continued

| Example | R1 | R2 | R3 | R4 |
|---------|----|----|----|----|
| 5 | 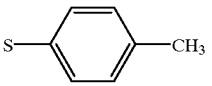 | 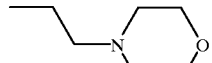 | 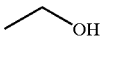 | H |
| 6 | 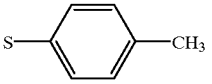 | 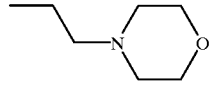 | 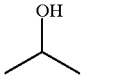 | H |
| 7 | 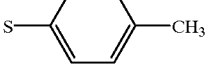 | 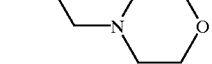 | 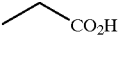 | H |
| 8 | 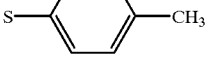 | 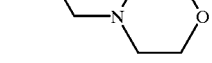 |  | H |
| 9 | 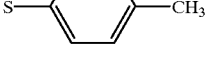 | 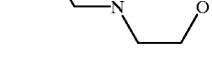 |  | H |
| 10 | 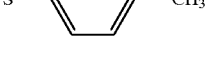 |  |  | H |
| 11 | 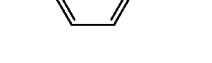 |  | 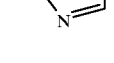 | H |
| 12 | 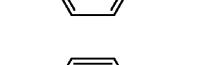 |  |  | H |
| 13 | 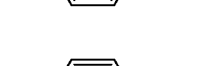 |  | 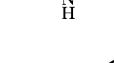 | H |
| 14 | 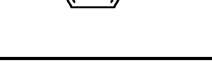 | 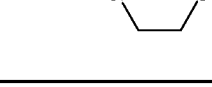 | 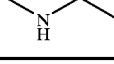 | H |

Treatment Process

A process for treating a host mammal having a condition associated with pathological matrix metalloprotease activity is also contemplated. That process comprises administering a compound described hereinbefore in an MMP enzyme-inhibiting effective amount to a mammalian host having such a condition. The use of administration repeated a plurality of times is particularly contemplated.

A contemplated compound is used for treating a host mammal such as a mouse, rat, rabbit, dog, horse, primate such as a monkey, chimpanzee or human that has a condition associated with pathological matrix metalloprotease activity.

Also contemplated is the similar use of a contemplated compound in the treatment of a disease state that can be affected by the activity of metalloproteases such as TNF-α convertase. Exemplary of such disease states are the acute phase responses of shock and sepsis, coagulation responses, hemorrhage and cardiovascular effects, fever and inflammation, anorexia and cachexia.

In treating a disease condition associated with pathological matrix metalloproteinase activity, a contemplated MMP inhibitor compound can be used, where appropriate, in the form of an amine salt derived from an inorganic or organic acid. Exemplary acid salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Also, a basic nitrogen-containing group can be quaternized with such agents as lower alkyl ($C_1$–$C_6$) halides, such as methyl, ethyl, propyl, and butyl chloride, bromides, and iodides; dialkyl sulfates like dimethyl, diethyl, dibuytl, and diamyl sulfates, long chain ($C_8$–$C_{20}$) halides such as decyl, lauryl, myristyl and dodecyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid.

Other compounds useful in this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Total daily dose administered to a host mammal in single or divided doses of an MMP enzyme-inhibiting effective amount can be in amounts, for example, of about 0.001 to about 30 mg/kg body weight daily and more usually about 0.01 to about 10 mg. Dosage unit compositions can contain such amounts or submultiples thereof to make up the daily dose. A suitable dose can be administered, in multiple sub-doses per day. Multiple doses per day can also increase the total daily dose, should such dosing be desired by the person prescribing the drug.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound useful in the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Preparation of Useful Compounds

Procedures are provided in the discussion and schemes that follow of exemplary chemical transformations that can be useful for the preparation of compounds of this invention. These syntheses, as with all of the reactions discussed herein, can be carried out under a dry inert atmosphere such a nitrogen or argon if desired. Selected reactions known to those skilled in the art, can be carried out under a dry atmosphere such as dry air whereas other synthetic steps, for example, aqueous acid or base ester or amide hydrolyses, can be carried out under laboratory air.

A contemplated compound can be prepared by a number of routes. In one generic route, an alpha-amine group of an amino acid is reacted with an aromatic sulfonyl halide, or the like, to form the corresponding sulfonamide.

The nitrogen substituent on the amino acid portion of the compounds of this invention can be varied. In addition, that variation can be accomplished at different stages in the synthetic sequence based on the needs and objectives of the skilled person preparing the compounds of this invention. The nitrogen side chain variations can include replacing the hydrogen substituent with a alkyl, arylalkyl, alkene or alkyne.

This can be accomplished by methods well known in the art such as alkylation of the amine with an electrophile such as halo- or sulfate ester (activated ester) derivative of the desired sidechain. An alkylation reaction is typically carried out in the presence of a base such as those discussed above and in a pure or mixed solvent as discussed above. A preferred base is postassium carbonate and a preferred solvent is DMF.

The alkenes, arylalkenes, arylalkynes and alkynes so formed can be reduced, for example, by hydrogenation with a metal catalyst and hydrogen, to an alkyl or arylalkyl compound of this invention and a alkyne or arylalkyne can be reduced to a alkene, arylalkene, arylakane or alkane with under catalytic hydrogenation conditions as discussed herein or with an deactivated metal catalyst. Catalysts can include, for example, Pd, Pd on Carbon, Pt, PtO$_2$ and the like. Less robust catalysts (deactivated) include such thing as Pd on BaCO$_3$ or Pd with quinoline or/and sulfur.

An alternative method for alkylation of the amine nitrogen is reductive alkylation. This process, well known in the art, allows treatment of the secondary amine with an aldehyde or ketone in the presence of a reducing agent such as borane, borane:THF, borane:pyridine, lithium aluminum hydride. Alternatively, reductive alkylation can be carried out under hydrogenation conditions in the presence of a metal catalyst. Catalysts, hydrogen pressures and temperatures are discussed and are well known in the art. A preferred reductive alkylation catalyst is borane:pyridine complex.

In the case where an intermediate is a carboxylic acid, standard coupling reactions well known in the art can be used to form the compounds of this invention including protected intermediates. For example, the acid can be converted into an acid chloride, mixed anhydride or activated ester and reacted with an alcohol, amine, hydroxylamine or a protected hydroxylamine in the presence of base to form the amide, ester, hydroxamic acid, protected hydroxamic acid. This is the same product as discussed above. Bases are discussed above and include N-methyl-morpholine, triethylamine and the like.

Coupling reactions of this nature are well known in the art and especially the art related to peptide and amino acid chemistry. Removal of the protecting group can be accomplished, if desired, using standard hydrolysis conditions such as base hydrolysis or exchange or acid exchange or hydrolysis as discussed.

The conversion of a carboxylic acid protected as an ester or amide into an hydroxamic acid derivative such as a O-arylalkylether or O-cycloalkoxyalkylether group such as the THP group is also contemplated. Methods of treating an acid or acid derivative with hydroxylamine or a hydroxylamine derivative to form a hydroxamic acid or hydroxamate derivative are discussed above. Hydroxylamine can be used in an exchange reaction by treatment of a precursor compound where the carboxyl is protected as an ester or amide with one or more equivalents of hydroxylamine hydrochloride or hydroxylamine at room temperature or above to provide a hydroxamic acid directly. The solvent or solvents, usually protic or protic solvent mixtures such as those listed herein.

This exchange process can be further catalyzed by the addition of additional acid. Alternatively, a base such as a salt of an alcohol used as a solvent, for example, sodium methoxide in methanol, can be used to form hydroxylamine from hydroxylamine hydrochloride in situ which can exchange with an ester or amide. As mentioned above, exchange can be carried out with a protected hydroxyl amine such as tetrahydropyranyl-hydroxyamine (THPONH$_2$), benzylhydroxylamine (BnONH$_2$), O-(trimethylsilyl) hydroxylamine and the like, in which case the compounds formed are tetrahydropyranyl (THP), benzyl (Bn) or TMS hydroxamic acid derivatives. Removal of the protecting groups when desired, for example, following further transformations in another part of the molecule or following storage, can be accomplished by standard methods well known in the art such as acid hydrolysis of the THP group as discussed above or reductive removal of the benzyl group with hydrogen and a metal catalyst such as palladium, platinum, palladium on carbon or nickel.

alpha-Amino acids or alpha-hydroxy carboxylic acids or protected carboxylic acids, hydroxamates or hydroxamic acid derivatives or intermediates (precursors) of this invention can themselves be prepared by displacing, for example, a halogen, sulfate ester or other electrophile, from the alpha carbon of an acid or a derivative as listed. Methods for the halogenation of acids, esters, acid chlorides and like are well known in the art and include, for example, the HVZ reaction, treatment with CuCl$_2$, N-bromo- or N-chloro-succinimide, I$_2$, carbon tetraiodide or bromide and the like. The halogen can be displaced with a nucleophile in an SN$_2$ reaction. Nucleophiles can include hydroxide, ammonia or amines.

Examples of bases that can be used include, for example, metal hydroxides such as sodium, potassium, lithium or magnesium hydroxide, oxides such as those of sodium, potassium, lithium, calcium or magnesium, metal carbonates such as those of sodium, potassium, lithium, calcium or magnesium, metal bicarbonates such as sodium bicarbonate or potassium bicarbonate, primary (I°), secondary (II°) or tertiary (III°) organic amines such as alkyl amines, arylalkyl amines, alkylarylalkyl amines, heterocyclic amines or heteroaryl amines, ammonium hydroxides or quaternary ammonium hydroxides. As non-limiting examples, such amines can include triethyl amine, trimethyl amine, diisopropyl amine, methyldiisopropyl amine, diazabicyclononane, tribenzyl amine, dimethylbenzyl amine, morpholine, N-methylmorpholine, N,N'-dimethylpiperazine, N-ethylpiperidine, 1,1,5,5-tetramethylpiperidine, dimethylaminopyridine, pyridine, quinoline, tetramethylethylenediamine and the like.

Non-limiting examples of ammonium hydroxides, usually made from amines and water, can include ammonium hydroxide, triethyl ammonium hydroxide, trimethyl ammonium hydroxide, methyldiiospropyl ammonium hydroxide, tribenzyl ammonium hydroxide, dimethylbenzyl ammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethyl ammonium hydroxide, tetramethyl ammonium hydroxide, dimethyldiiospropyl ammonium hydroxide, benzymethyldisopropyl ammonium hydroxide, methyldiazabicyclononyl ammonium hydroxide, methyltribenzyl ammonium hydroxide, N,N-dimethylmorpholinium hydroxide, N,N,N',N'-tetramethylpiperazenium hydroxide, and N-ethyl-N'-hexylpiperidinium hydroxide and the like. Metal hydrides, amide or alcoholates such as calcium hydride, sodium hydride, potassium hydride, lithium hydride, sodium methoxide, potassium tert-butoxide, calcium ethoxide, magnesium ethoxide, sodium amide, potassium diisopropyl amide and the like can also be suitable reagents. Organometallic deprotonating agents such as alkyl or aryl lithium reagents such as methyl, phenyl, butyl, iso-butyl, sec-butyl or tert-butyl lithium, nodium or potassium salts of dimethylsulfoxide, Grignard reagents such as methylmagnesium bromide or methymagnesium chloride, organocadium reagents such as dimethylcadium and the like can also serve as bases for causing salt formation or catalyzing the reaction. Quaternary ammonium hydroxides or mixed salts are also useful for aiding phase transfer couplings or serving as phase transfer reagents. Preferred base for use in the alkylation reaction is lithium diisopropyl amide as mentioned above.

Reaction media in general can be comprised of a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, iso-propanol and the like.

Typical non-protic solvents include acetone, tetrahydrofurane (THF), dioxane, diethylether, tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, nitromethane, tetramethylurea, N-methylpyrrolidone and the like.

Non-limiting examples of reagents that can be used as solvents or as part of a mixed solvent system include organic or inorganic mono- or multi-protic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols or amines for making esters or amides or thiols for making the products of this invention and the like. Room temperature or less or moderate warming (−10° C. to 60° C.) are the preferred temperatures of the reaction. If desired, the reaction temperature might be about 78° C. to the reflux point of the reaction solvent or solvents. The preferred solvent for an alkylation reaction is tetrahydrofurane (THF).

Acids are used in many reactions during various synthesis. The Schemes as well as this discussion preparative methods illustrate acid use for the removal of the THP protecting group to produce a hydroxamic acid, removal of a tert-butoxy carbonyl group, hydroxylamine/ester exchange and the like. Acid hydrolysis of carboxylic acid protecting groups or derivatives is well known in the art. These methods, as is well known in the art, can use acid or acidic catalysts. The acid can be mono-, di- or tri-protic organic or inorganic acids. Examples of acids include hydrochloric acid, phosphoric acid, sulfuric acid, acetic acid, formic acid, citric acid, succinic acid, hydrobromic acid, hydrofluoric acid, carbonic acid, phosphorus acid, p-toluene sulfonic acid, trifluoromethane sulfonic acid, trifluoroacetic acid, difluoroacetic acid, benzoic acid, methane sulfonic acid, benzene sulfonic acid, 2,6-dimethylbenzene sulfonic acid, trichloroacetic acid, nitrobenzoic acid, dinitrobenzoic acid, trinitrobenzoic acid, and the like. They can also be Lewis acids such as aluminum chloride, borontrifluoride, antimony pentafluoride and the like.

Contemplated compounds can include compounds wherein a nitrogen of an amine is acylated to provide, for example, amino acid carbamates. Non-limiting examples of these carbamates are the carbobenzoxycarbonyl (Z, CBZ, benzyloxycarbonyl), iso-butoxycarbonyl and tert-butoxycarbonyl (BOC, t-BOC) compounds. The materials can be made, as discussed above, at various stages in the synthesis based on the needs and decisions made by a person skilled in the art using methods well know in the art.

Useful synthetic techniques and reagents include those used in protein, peptide and amino acid synthesis, coupling and transformation chemistry. The use of the tert-butoxycarbonyl (BOC) and benzyloxycarbonyl (Z) as will as their synthesis and removal are examples of such protection or synthesis schemes. Transformations of amino acids, amino esters, amino acid hydroxamates, amino acid hydroxamate derivatives and amino acid amides of this invention or compounds used in this invention is discussed herein or/and shown in the schemes. This includes, for example, active ester or mixed anhydride couplings wherein preferred bases, if required, are tertiary amines such as N-methylmorpholine. Reagents for protection of the amine group of the protected amino acids include carbobenzoxy chloride, iso-butylchloroformate, tert-butoxycarbonyl chloride, di-tert-butyl dicarbonate and the like which are reacted with the amine in non-protic or dipolar aprotic solvents such as DMF or THF or mixtures of solvents.

Removal of protecting groups such as carbamates, silyl groups and benzyl, p-methoxybenzyl, or other substituted benzyl groups or diphenylmethyl (benzhydryl) or triphenylmethyl (trityl) can be carried out at different stages in the synthesis of the compounds of this invention as required by methods selected by one skilled in the art. These methods are well known in the art including the amino acid, amino acid coupling, peptide synthesis, peptide mimetic synthesis art. Removal methods can include catalytic hydrogenation, base hydrolysis, carbonyl addition reactions, acid hydrolysis and the like. Both the preparation and removal of protecting groups, for example, carbamates, benzyl groups and/or substitued arylalkyl groups is discussed in Green, T., *Protecting Groups in Organic Chemistry*, Second ed., John Wiley & Sons, New York (1991). A preferred method of removal of a BOC group is HCl gas in methylene chloride which, following normal workup, provides directly an HCl salt of an aminoacid of this invention.

Salts of the compounds or intermediates of this invention are prepared in the normal manner wherein acidic compounds are reacted with bases such as those discussed above to produce metal or nitrogen containing cation salts. Basic compounds such as amines can be treated with an acid to form an amine salt.

Compounds of the present can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes well known in the art, for example by formation of diastereoisomeric salts by treatment with an optically active acid or base.

Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers.

Still another available method involves synthesis of covalent diastereoisomeric molecules, e.g., esters, amides, acetals, ketals, and the like, by reacting compounds of Formula I with an optically active acid in an activated form, a optically active diol or an optically active isocyanate. The synthesized diastereoisomers can be separated by conventional means such as chromatography, distillation, crystallization or sublimation, and then hydrolyzed to deliver the enantiomericaly pure compound. In some cases hydrolysis to the parent optically active drug is not necessary prior to dosing the patient since the compound can behave as a prodrug. The optically active compounds of Formula I can likewise be obtained by utilizing optically active starting materials.

In addition to the optical isomers or potentially optical isomers discussed above, other types of isomers are specifically intended to be included in this discussion and in this invention. Examples include cis isomers, trans isomers, E isomers, Z isomers, syn-isomers, anti-isomers, tautomers and the like. Aryl, heterocyclo or heteroaryl tautomers, heteroatom isomers and ortho, meta or para substitution isomers are also included as isomers. Solvates or solvent addition compounds such as hydrates or alcoholates are also specifically included both as chemicals of this invention and in, for example, formulations or pharmaceutical compositions for drug delivery.

Where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure. For example, two hydroxyl groups, two amino groups, two thiol groups or a mixture of two hydrogen-heteroatom groups on the same carbon are known not to be stable without protection or as a derivative.

The chemical reactions described above are generally disclosed in terms of their broadest application to the preparation of the compounds of this invention. Occasionally, the reactions can not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Other compounds of this invention that are acids can also form salts. Examples include salts with alkali metals or alkaline earth metals, such as sodium, potassium, calcium or magnesium or with organic bases or basic quaternary ammonium salts Hydroxamate compounds of the present invention can be prepared according to, for example, Scheme I. In that Scheme, amino acid 1 is treated with 4-fluorophenylsulfonyl chloride in the presence of triethylamine to afford sulfonamide 2. Treatment of 2 with isobutylene under acid catalysis gives the tert-butyl ester 3. Reaction of the fluoroaryl derivative 3 with the appropriate thiol in the presence of either potassium carbonate or cesium carbonate affords the product of nucleophilic aromatic displacement 4, which is treated with an appropriate alkylating agent in the presence of potassium carbonate to give the alkylated sulfonamide 5. An example of an alkylating agent is {(2-N-morpholinylethylchloride) or (N-[2-(4-morpholinyl) ethylchloride])}. Hydrolysis of the tert-butyl ester of 5 affords carboxylic acid 6 which is coupled with O-tetrahydro-2H-pyran-2-yl-hydroxylamine under standard coupling conditions to afford THP-protected hydroxamate 7. Removal of the THP protecting group under acidic conditions affords the requisite hydroxamic acid 8.

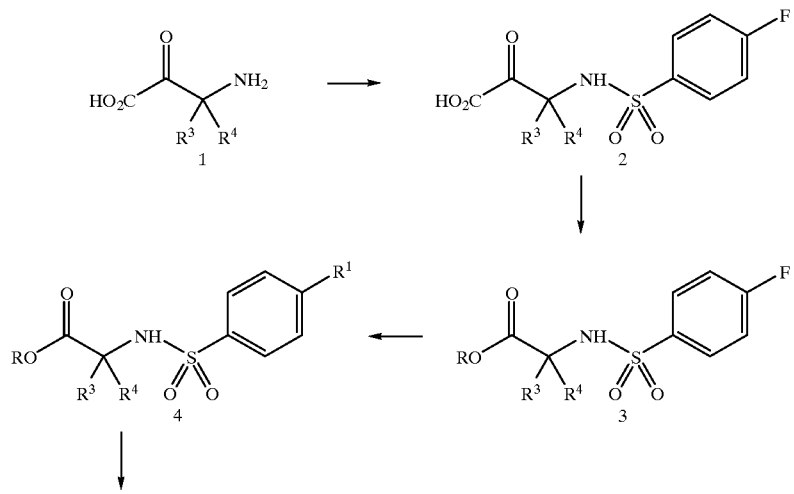

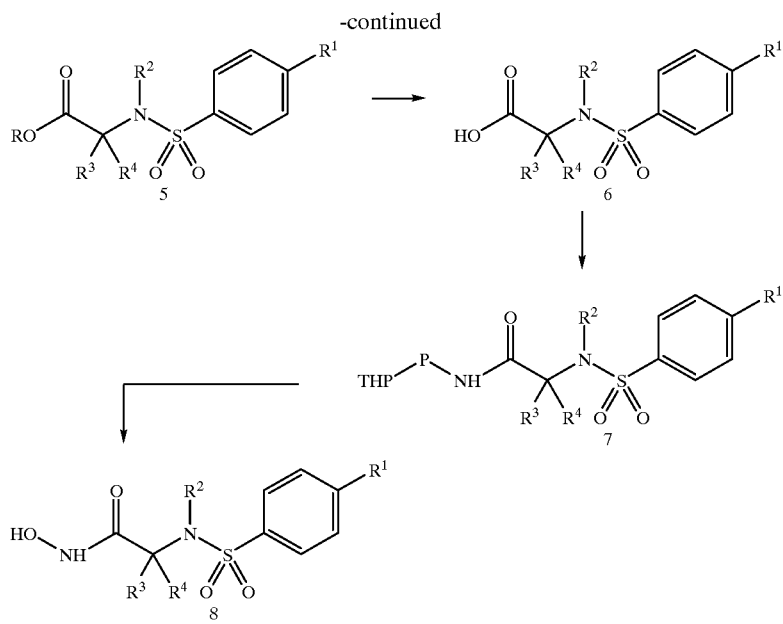

Alternately, hydroxamate compounds of the present invention can be prepared according to Scheme II. In this case sulfonamide carboxylic acid 2 is esterified under standard conditions to afford an ester 9. Reaction of 9 with the appropriate thiol in the presence of either potassium carbonate or cesium carbonate affords the sulfide 10, which is treated with an appropriate alkylating agent in the presence of potassium carbonate to give the alkylated sulfonamide 11. Reaction of the methyl ester 11 then affords the hydroxamate product 8.

Compounds of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes well known in the art, for example by formation of diastereoisomeric salts by treatment with an optically active acid or base. Examples of appropriate acids are tartaric, diacetyltartaric, dibenzoyltartaric, ditoluoyltartaric and camphorsulfonic

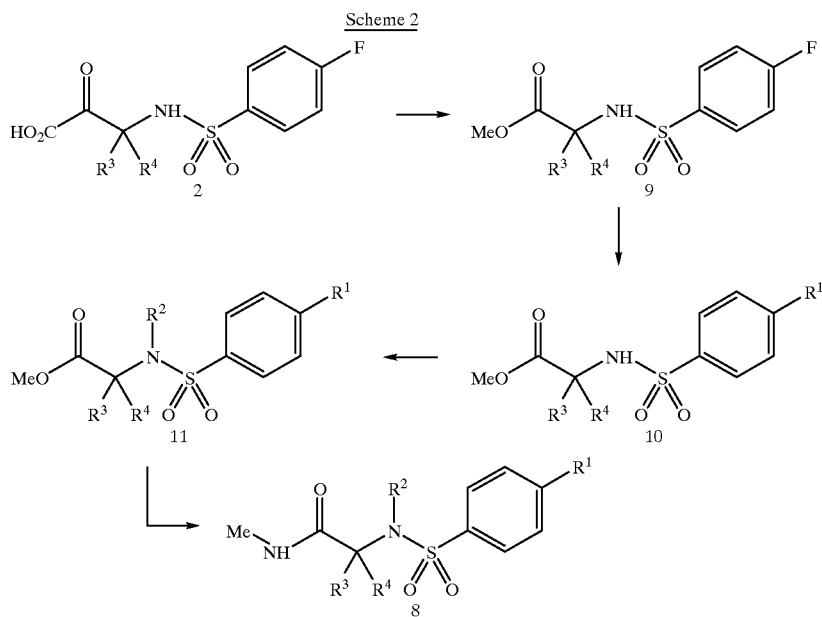

Oxidation of sulfides or sulfoxides of this invention can be accomplished using reagents such as hydrogen peroxide, sodium metaperiodate, persulfate salts, tert-butylperoxide, peracetic acid and the like.

acid and then separation of the mixture of diastereoisomers by crystallization followed by liberation of the optically active bases from these salts. A different process for separation of optical isomers involves the use of a chiral chromatography column optimally chosen to maximize the separation of the enantiomers.

Still another available method involves synthesis of covalent diastereoisomeric molecules, e.g., esters, amides, acetals, ketals, and the like, by reacting compounds of Formula I with an optically active acid in an activated form, a optically active diol or an optically active isocyanate. The synthesized diastereoisomers can be separated by conventional means such as chromatography, distillation, crystallization or sublimation, and then hydrolyzed to deliver the enantiomericaly pure compound. In some cases, hydrolysis to the parent optically active drug is not necessary prior to dosing the patient since the compound can behave as a prodrug. The optically active compounds of Formula I can likewise be obtained by utilizing optically active starting materials.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Best Mode for Carrying Out the Invention

Without further elaboration, it is believed that one skilled in the art can, using the preceding description, utilize the present invention to its fullest extent. The following specific embodiments are, therefore, to be construed as merely illustrative, and not limitative of the remainder of the disclosure in any way whatsoever.

EXAMPLE 1a

N-[(4-fluorophenyl)sulfonyl]-D-valine

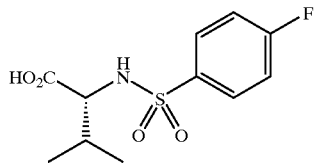

To a solution of D-valine (6.40 g, 54.6 mmol) in $H_2O$ (62 mL) and acetone (25 mL) was added triethylamine (16.2 mL, 117 mmol). The solution was cooled to zero degrees C. in an ice/$H_2O$ bath and a solution of 4-fluorobenzenesulfonyl chloride (10.0 g, 51.4 mmol) in acetone (25 mL) was added dropwise. After stirring at room temperature for 20 hours, the resulting yellow solution was concentrated in vacuo to remove the acetone. The aqueous residue was extracted with toluene (2×50 mL) and acidified to pH=1 with 12 M HCl. The solution was extracted with ethyl acetate (3×50 mL) and the combined organic layers were washed successively with 1M $KHSO_4$ (50 mL), $H_2O$ (50 mL), and sat'd NaCl (50 mL), then dried over $MgSO_4$. Concentration in vacuo and trituration with hexane afforded N-[(4-fluorophenyl)-sulfonyl]-D-valine as a white solid (12.56 g, 89%): MS MH+ calcd. for Anal. Calc'd for $C_{11}H_{14}NO_4SF$: C, H, N. Found: C, H, N. HR mass calculated for $C_{11}H_{14}NO_4S$: 276.0706. Found: 276.0710.

EXAMPLE 1b

N-[(4-fluorophenyl)sulfonyl]-D-valine, 1,1-dimethylethyl ester

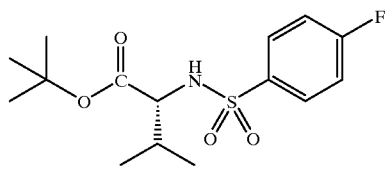

A solution of N-[(4-fluorophenyl)-sulfonyl]-D-valine from Example 1a (8.00 g, 29.1 mmol) in $CH_2Cl_2$/dioxane was treated with isobutylene in the presence of $H_2SO_4$ at room temperature at a pressure of 18 psi. The reaction was quenched by adding the solution to a mixture of $NaHCO_3$ (20 g) in water (300 mL) cooled in an ice bath. The mixture was extracted with ethyl acetate. The ethyl acetate layers were combined and washed with $H_2O$ and brine, dried over $MgSO_4$, and concentrated to a solid. Recrystallization from diethyl ether/hexane afforded N-[(4-fluorophenyl)-sulfonyl]-D-valine, 1,1-dimethylethyl ester, as a white solid (6.99 g, 73%): MS MH+ calc'd for $Cl_5H_{22}NO_4SF$: 332, found: 332. Anal. calc'd for $Cl_5H_{22}NO_4SF$: C, 54.36; H, 6.69; N, 4.23. Found: C, 54.21; H, 6.86; N, 4.14.

EXAMPLE 1c

N-[[4-[(3-methylphenyl)thio]phenyl]sulfonyl]-D-valine, 1,1-dimethylethyl ester

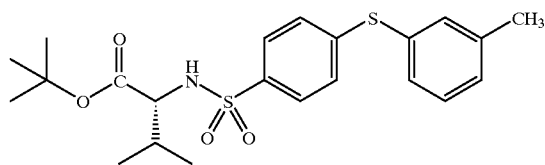

To a solution of N-[(4-fluorophenyl)-sulfonyl]-D-valine, 1,1-dimethylethyl ester, from Example 1b (3.0 g, 9.06 mmol) in 35 mL DMF was added m-thiocresol (3.23 mL, 27.2 mmol) and powdered $K_2CO_3$ (3.76 g, 27.2 mmol). The mixture was heated to 70° C. for 20 hours. After cooling to room temperature, the solution is washed with $H_2O$ (4×100 mL), and sat'd NaCl (2×100 mL), and dried over $Mg_2SO_4$. After concentration in vacuo, the residue was purified by flash chromatography (10:90 EtOAc/hexane) to afford N-[[4-[(3-methylphenyl)thio]phenyl]sulfonyl]-D-valine, 1,1-dimethylethyl ester, as a white solid (3.95 g, quantitative yield): MS MH+ calc'd for $C_{22}H_{29}NO_4S_2$: 436, found: 436. Anal. calc'd for $C_{22}H_{29}NO_4S_2$: C, 60.66; H, 6.71; N, 3.22; Found: C, 60.57; H, 6.47; N, 3.14.

EXAMPLE 1d

N-[[4-[(3-methylphenyl)thio]phenyl]sulfonyl]-N-[2-(4-morpholinyl)ethyl]-D-valine, 1,1-dimethylethyl ester

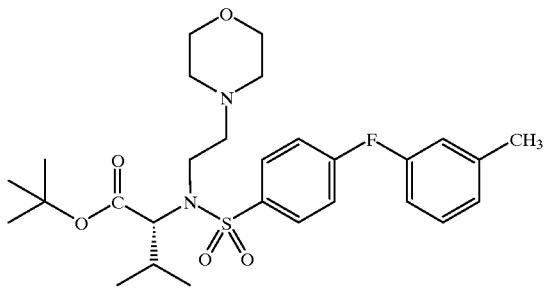

To a solution of N-[[4-[(3-methylphenyl)thio]phenyl]sulfonyl]-D-valine, 1,1-dimethylethyl ester, from Example 1c (3.96 g, 9.08 mmol) in 30 mL DMF was added 4-(2-chloroethyl)-morpholine hydrochloride (5.07 g, 27.2 mmol) and K$_2$CO$_3$ (3.76 g, 27.2 mmol). The solution was heated to 63° C. for 24 hours. Additional K$_2$CO$_3$ (1.25 g, 9.08 mmol) and 4-(2-chloroethyl)-morpholine hydrochloride (1.69 g, 9.08 mmol) was added and the mixture heated for an additional 24 hours at 63° C. The mixture was then partitioned between ethyl acetate and H$_2$O, and the organic was washed with sat'd NaCl (3×30 mL) and dried over MgSO$_4$. After concentration in vacuo, the residue was purified by flash chromatography (20:80 hexane/EtOAc) to afford N-[[4-[(3-methylphenyl)thio]phenyl]sulfonyl)-N-[2-(4-morpholinyl)ethyl]-D-valine, 1,1-dimethylethyl ester, as a white solid (5.21 g): MS MH+ calc'd for C$_{28}$H$_{41}$N$_2$O$_5$S$_2$: 549, found: 549. HRMS calc'd for C$_{28}$H$_{41}$N$_2$O$_5$S$_2$: 548.2379; found: 548.2384.

EXAMPLE 1e

N-[[4-[(3-methylphenyl)thio]phenyl]sulfonyl]-N-[2-(4-morpholinyl)ethyl]-D-valine, monohydrochloride (E)

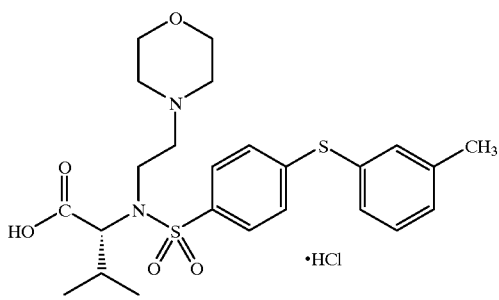

A solution of N-[[4-[(3-methylphenyl)thio]phenyl]sulfonyl]-N-[2-(4-morpholinyl)ethyl]-D-valine, 1,1-dimethylethyl ester, from Example 1d (5.21 g, 9.08 mmol) in 12 M HCl (30 mL) and H$_2$O (30 mL) was stirred at room temperature for 30 minutes and then heated to reflux for 25 minutes. Concentration in vacuo afforded N-[[4-[(3-methylphenyl)thio]phenyl]sulfonyl]-N-[2-(4-morpholinyl) ethyl]-D-valine, monohydrochloride, as a white solid (5.30 g). MS MH+ calc'd for C$_{24}$H$_{33}$N$_2$O$_5$S$_2$: 494, found: 494. HRMS calc'd for C$_{24}$H$_{33}$N$_2$O$_5$S$_2$: 493.1831; found: 493.1833.

EXAMPLE 1f 3-methyl-2R-[[[4-[(3-methylphenyl)thio]phenyl]-sulfonyl]-[2-(4-morpholinyl)ethyl]amino]-N-[(tetrahydro-2H-pyran-2-yl)oxy]butanamide

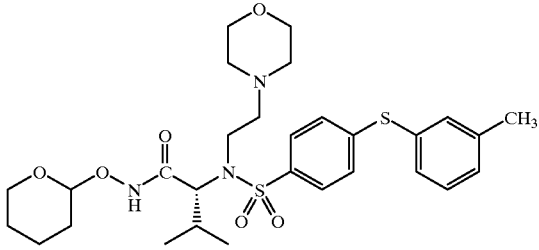

To a solution of N-[[4-[(3-methylphenyl)thio]phenyl] sulfonyl]-N-[2-(4-morpholinyl)ethyl]-D-valine, monohydrochloride, from Example 1e (5.30 g, 9.08 mmol), 4-methylmorpholine (3.99 mL, 36.3 mmol), N-hydroxybenzothiazole (1.47 g, 10.9 mmol), and N-(3-dimethylaminopropyl)-N'-ethylcarbodiimide hydrochloride (EDC) (2.44 g, 12.7 mmol) in DMF (50 mL) was added O-tetrahydro-2H-pyran-2-yl-hydroxylamine (1.60 g, 13.6 mmol) and was stirred for 3 hours under an argon atmosphere. The solution was diluted with H$_2$O and extracted into ethyl acetate (3×). The organic layer was washed with sat'd NaCl (2×50 mL) and dried over MgSO$_4$. After concentration in vacuo, the residue was purified by flash chromatography (40:60 acetone/hexane) to afford 3-methyl-2R-[[[4-[(3-methylphenyl)thio]phenyl]sulfonyl]-[2-(4-morpholinyl)ethyl]amino]-N-[(tetrahydro-2H-pyran-2-yl)oxy]butanamide as an oil (3.60 g, 67%): MS MH+ calc'd for C$_{29}$H$_{41}$N$_3$O$_6$S$_2$: 592, found: 592. Anal. calc'd for C$_{29}$H$_{41}$N$_3$O$_6$S$_2$: C, 58.86; H, 6.98; N, 7.10; found: C, 58.45; H, 7.34; N, 6.71.

EXAMPLE 1g

N-hydroxy-3-methyl-2R-[[[4-[(3-methylphenyl)thio] phenyl]sulfonyl]-[2-(4-morpholinyl)-ethyl]amino] butanamide, monohydrochloride

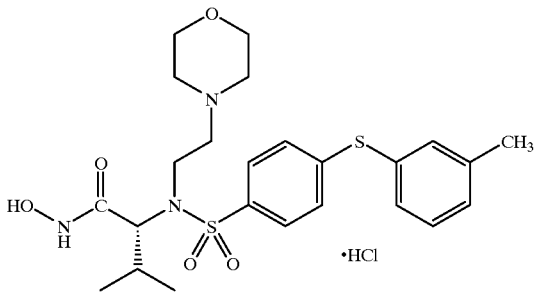

A solution of 3-methyl-2R-[[[4-[(3-methylphenyl)thio] phenyl]-sulfonyl]-[2-(4-morpholinyl)ethyl]amino]-N-[(tetrahydro-2H-pyran-2-yl)oxy]butanamide from Example 1f in methanol (50 mL) was cooled to zero degrees C. in an ice water bath and HCl was bubbled into the solution for 15 minutes. The solution was then concentrated under a stream of N$_2$. The residue was dissolved into a minimal amount of ethanol and added dropwise to stirring diethyl ether. Vacuum filtration yielded the title compound as a white solid (2.88 g, 87%): MS MH+ calc'd for C$_{24}$H$_{33}$N$_3$O$_5$S$_2$: 508 (MH+).

HRMS calc'd for $C_{24}H_{34}N_3O_5S_2$: 508.1940; found: 508.1965. Anal. calc'd for $C_{24}H_{33}N_3O_5S_2 \cdot HCl \cdot H_2O$: C, 51.28; H, 6.46; N, 7.47; S, 11.41; Cl, 6.31; found: C, 50.83; H, 6.17; N, 7.29; S, 11.48; Cl, 6.64.

EXAMPLE 2a

N-[[4-[(4-methylphenyl)thio]phenyl]sulfonyl]-D-valine, 1,1-dimethylethyl ester

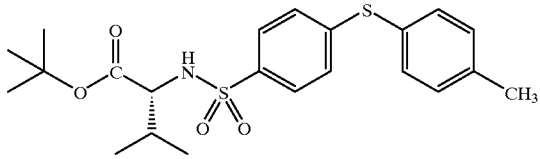

To a solution of N-[(4-fluorophenyl)-sulfonyl]-D-valine, 1,1-dimethylethyl ester (the title compound of Example 1b; 1.95 g, 5.9 mmole) in DMF (50 ml) was added potassium carbonate (2.44 g, 17.8 mmol) and p-thiocresol (2.2 g, 17.8 mmol) and the resulting solution was stirred at 68° C. for 18 hours. The solution was cooled to ambient temperature, water was added, and extracted with ethyl acetate. The combined extracts were washed successively with water and brine, dried over magnesium sulfate and concentrated to give an oil which was chromatographed on silica gel eluting with 15% ethyl acetate/hexane to give N-[[4-[(4-methylphenyl)thio]phenyl]sulfonyl]-D-valine, 1,1-dimethylethyl ester (2.5 g, 98%): anal. calc'd for $C_{22}H_{29}NS_2O_4$: C, 60.66; H, 6.71; N, 3.22; S, 14.72. Found: C, 60.45; H, 7.08; N, 3.17; S, 14.90. MS MH+ calc'd for $C_{22}H_{29}NS_2O_4$: 436, found 436.

EXAMPLE 2b

N-[[4-[(4-methylphenyl)thio]phenyl]sulfonyl]-N-[2-(4-morpholinyl)ethyl]-D-valine, 1-dimethylethyl ester

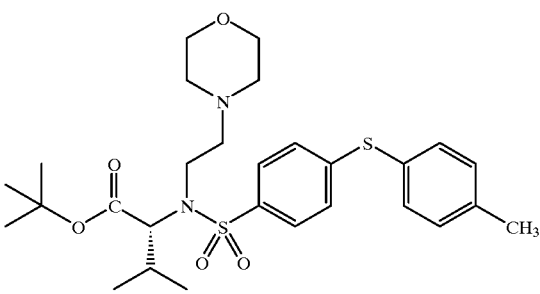

To a solution of N-[[4-[(4-methylphenyl)thio]-phenyl]sulfonyl]-D-valine, 1,1-dimethylethyl ester, from Example 2a (2.4 g ,5.5 mmole) in DMF (50 ml) was added potassium carbonate (2.28 g, 16.5 mmole) and 4-(2-chloroethyl) morpholine hydrochloride (3.07 g, 16.5 mmole). After vigorously stirring at 60° C. for 18 hours, the reaction was worked up by adding water and extracting with ethyl acetate. The combined organic extracts were washed with water, brine, dried (MgSO$_4$), filtered and concentrated in vacuo to give an oil which was purified on silica gel eluting with 50/50 ethyl acetate/hexane to give N-[[4-[(4-methylphenyl) thio]phenyl]sulfonyl]-N-[2-(4-morpholinyl)-ethyl]-D-valine, 1,1-dimethylethyl ester (3.62 g, 100%): anal. calc'd for $C_{28}H_{40}N_2S_2O_5$: C, 61.28; H, 7.35; N, 5.10. Found: C, 61.12; H. 7.69; N, 4.91. HRMS MH+ calc'd for $C_{28}H_{40}N_2S_2O_5$: 548.2379, found: 548.2386.

EXAMPLE 2c

N-[[4-[(4methylphenyl)thio]phenyl]sulfonyl]-N-[2-(4-morpholinyl)ethyl]-D-valine, monohydrochloride

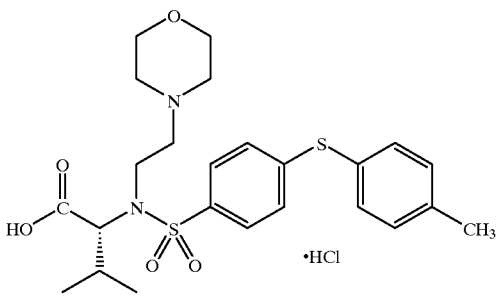

To a suspension of N-[[4-[(4-methylphenyl)thio]-phenyl] sulfonyl]-N-[2-(4-morpholinyl)ethyl]-D-valine, 1,1-dimethylethyl ester, from Example 2b (3.5 g, 6.4 mmole) in water (50 ml) was added concentrated HCl (50 ml). After stirring for 1 hour at room temperature for 30 minutes under reflux, the reaction was concentrated to give N-[[4-[(4-methylphenyl)thio]phenyl]sulfonyl]-N-[2-(4-morpholinyl)-ethyl]-D-valine, monohydrochloride, as a white foam (3.5 g, 100%): MS MH+ calc'd for $C_{24}H_{32}N_2S_2O_5$; 493, found: 493.

EXAMPLE 2d 3-methyl-2R-[[[4-[(4-methylphenyl)thio]phenyl]sulfonyl][2-(4-morpholinyl)ethyl]amino]-N-[(tetrahydro-2H-pyran-2-yl)oxy]butanamide

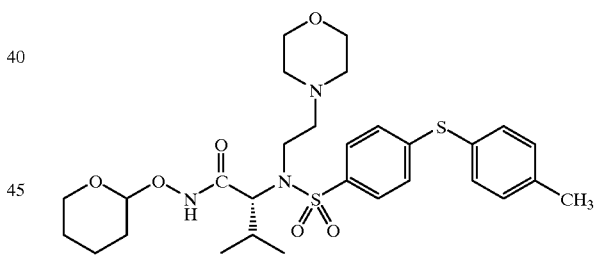

To a solution of N-[[4-[(4-methylphenyl)thio]phenyl] sulfonyl]-N-[2-(4-morpholinyl)-ethyl]-D-valine, monohydrochloride, from Example 2c (3.5 g, 6.6 mmol)in DMF (50 ml) was added triethylamine (2.9 ml, 26.4 mmol), N-methyl morpholine (1.07 g, 7.9 mmol), 1-(3-dimethylaminopropyl)-3-ethyl carbodiimide hydrochloride (1.77 g, 9.2 mmol), and O-tetrahydro-2H-pyran-2-yl-hydroxylamine (1.16 g, 9.9 mmol). After stirring for 18 hours at room temperature, water was added to the reaction mixture, and extracted with ethyl acetate. The combined extracts were washed successively with water, brine, dried (MgSO$_4$), filtered and concentrated under reduced pressure to give an oil which was chromatographed on silica gel eluting with 20% acetone/hexane to give 3-methyl-2R-[[[4-[(4-methylphenyl)thio]phenyl]sulfonyl][2-(4-morpholinyl) ethyl]amino]-N-[(tetrahydro-2H-pyran-2-yl)oxy] butanamide as a diasteriomeric mixture (2.3 g, 57%): HRMS for $C_{29}H_{42}N_3S_2O_6$: 592.2515, found: 592.2554.

EXAMPLE 2e

N-hydroxy-3-methyl-2R-[[[4-[(4-methylphenyl)thio]phenyl]sulfonyl][2-(4-morpholinyl)ethyl]-amino]butanamide, monohydrochloride

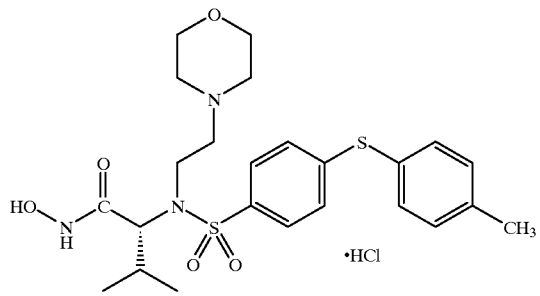

To A solution of solution of 3-methyl-2R-[[[4-[(4-methylphenyl)thio]phenyl]sulfonyl][2-(4-morpholinyl)-ethyl]amino]-N-[(tetrahydro-2H-pyran-2-yl)oxy] butanamide from Example 2d (2.3 g, 3.9 mmol) in methanol (50 ml), cooled to zero degrees C., was bubbled HCl for 20 minutes. The solution was concentrated in vacuo to give a foam which was dissolved in methanol (1 ml) and added dropwise to a large volume of ethyl ether (600 ml) with vigorous stirring. The resulting solid was filtered to give N-hydroxy-3-methyl-2R-[[[4-[(4-methylphenyl)thio]phenyl]sulfonyl][2-(4-morpholinyl)ethyl]amino]butanamide, monohydrochloride, (1.84 g, 88%): anal. calc'd for $C_{24}H_{33}N_3S_2O_5 \cdot HCl \cdot H_2O$: C, 52.11, H, 6.38, N, 7.60, S, 11.59. Found: C, 51.90, H, 6.16, N, 7.43, S, 11.83.

EXAMPLE 3a

N-[(4-fluorophenyl)sulfonyl]-D-alanine

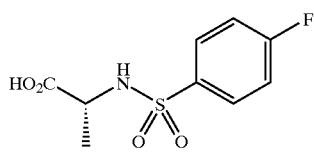

A solution of D-alanine (9.73 g, 0.109 mole) and triethylamine (32.6 mL, 0.234 mol) in water (124 mL) and acetone (50 mL) was cooled to zero degrees C. 4-Fluorobenzenesulfonyl chloride (20.0 g, 0.103 mol) in acetone (50 mL) was added dropwise over 1 minute. This solution was allowed to warm to room temperature and stirred overnight. The solution was concentrated to remove the acetone. The aqueous residue was washed with toluene and then acidified to about pH=1 with 12 N HCl and then extracted with ethyl acetate. The combined ethyl acetate layers were washed successively with 1 N aqueous $KHSO_4$ solution, $H_2O$, and brine. After drying with $MgSO_4$, the filtrate was concentrated to a white solid (23.3 g, 92% yield). The proton NMR spectrum was consistent with N-[(4-fluorophenyl)sulfonyl]-D-alanine. Elemental anal. calc'd for $C_9H_{10}NO_4FS$: C, 43.72; H, 4.08; N, 5.67. Found: C, 43.99; H, 3.97; N, 5.68.

EXAMPLE 3b

N-[(4-fluorophenyl)sulfonyl]-D-alanine, 1,1-dimethylethyl ester

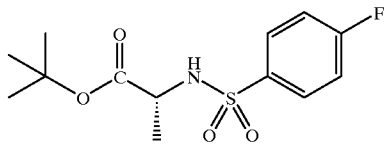

A solution of N-[(4-fluorophenyl)sulfonyl]-D-alanine from Example 3a (8.00 g, 32.4 mmol), isobutene (120 mL), and concentrated sulfuric acid (0.5 mL) in 1,4-dioxane (20 mL) and $CH_2Cl_2$ (60 mL) was added to a 500 mL high pressure bottle and sealed. The mixture was shaken at room temperature for 95 hours at a pressure of 18 psi. The mixture was poured into an aqueous solution containing 20 g of sodium bicarbonate, which was cooled by an ice bath. The aqueous solution was extracted with ethyl acetate and the combined organic layers were washed successively with water and brine, dried with $MgSO_4$, and concentrated to a clear, yellow oil (6.06 g). Chromatography on silica gel (20% ethyl acetate in hexane) afforded N-[(4-fluorophenyl)sulfonyl]-D-alanine, 1,1-dimethylethyl ester, as a white solid (5.00 g, 51% yield): Anal. calc'd for $C_{13}H_{18}NO_4FS$: C, 51.47; H, 5.98; N, 4.62. Found: C, 51.39; H, 5.82; N, 4.53.

EXAMPLE 3c

N-[[4-(phenylthio)phenyl]sulfonyl]-D-alanine, 1,1-dimethylethyl ester

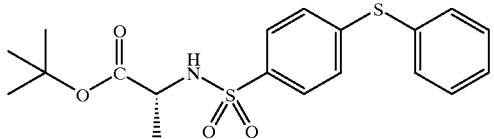

A mixture of N-[(4-fluorophenyl)-sulfonyl]-D-alanine, 1,1-dimethylethyl ester, from Example 3b (4.98 g, 16.4 mmol), thiophenol (5.05 mL, 49.2 mmol), and potassium carbonate (6.80 g, 49.2 mmol) in dry DMF (48 mL) was heated with a 70° C. oil bath overnight. The mixture was cooled to room temperature and poured into a mixture of water (700 mL) and toluene (250 mL). The pH to of the aqueous layer was acidified with concentrated HCl. The aqueous layer was extracted with toluene (2×250 mL) and the combined toluene layers were washed with water and brine, dried over $MgSO_4$, and concentrated to a clear, orange oil (6.28 g). Chromatographic purification (25% ethyl acetate in hexane) afforded a white solid (5.35 g, 83% yield). The proton NMR was consistent for N-[[4-(phenylthio)phenyl]sulfonyl]-D-alanine, 1,1-dimethylethyl ester: anal. calc'd for $C_{19}H_{23}NO_4S_2$: C, 57.99; H, 5.89; N, 3.56. Found: C, 58.02; H, 6.04; N, 3.47.

EXAMPLE 3d

N-[2-(4-morpholinyl)ethyl]-N-[[4-(phenylthio)-phenyl]sulfonyl]-D-alanine, 1,1-dimethylethyl ester

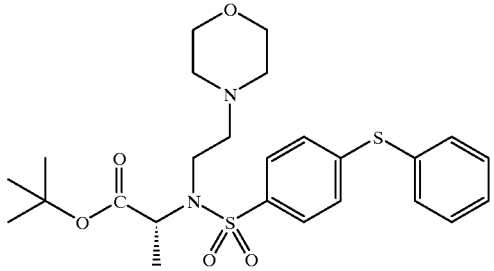

A mixture of N-[[4-(phenylthio)phenyl]sulfonyl]-D-alanine, 1,1-dimethylethyl ester, from Example 3c (1.06 g, 2.69 mmol), 4-(2-chloroethyl)morpholine hydrochloride (7.51 g, 40.4 mmol), and potassium carbonate (7.46 g, 54.0 mmol) in dry DMF (40 mL) was heated with a 70° C. oil bath overnight. The room temperature mixture was poured into water and extracted with ethyl acetate. The combined ethyl acetate layers were washed with water and brine, dried with MgSO$_4$, and concentrated to a white paste. The paste was triturated with hexane to afford a white solid (5.28 g), which was purified by chromatography (45% methyl tert-butyl ether in toluene) to give the title compound (4.38 g, 64%) as a white solid. The proton NMR was consistent with N-[2-(4-morpholinyl)ethyl]-N-[[4-(phenylthio)phenyl]sulfonyl]-D-alanine, 1,1-dimethylethyl ester: anal. calc'd for C$_{25}$H$_{34}$N$_2$O$_5$S$_2$: C, 59.26; H, 6.76; N, 5.53. Found: C, 59.21; H, 6.68; N, 5.32.

EXAMPLE 3e

N-[2-(4-morpholinyl)ethyl]-N-[[4-(phenylthio)-phenyl]sulfonyl]-D-alanine, monohydrochloride

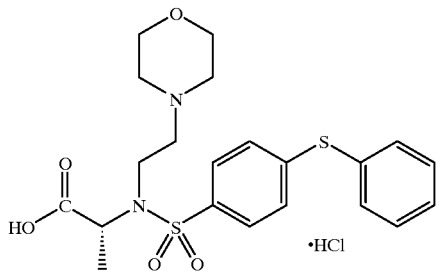

N-[2-(4-morpholinyl)ethyl]-N-[[4-(phenylthio)-phenyl]sulfonyl]-D-alanine, 1,1-dimethylethyl ester from Example 3d (4.33 g, 8.55 mmol) in 6 N HCl (71 mL) was refluxed for 20 minutes, and upon cooling to room temperature a white solid precipitated. The solid was collected, washed with water, and dried in a 40° C. vacuum oven to give N-[2-(4-morpholinyl)ethyl]-N-[[4-(phenylthio)-phenyl]sulfonyl]-D-alanine, monohydrochloride, as a white solid (2.38 g, 57% yield): anal. calc'd for C$_{21}$H$_{26}$N$_2$O$_5$S$_2$.1.2HCl: C, 51.02; H, 5.55; N, 5.67. Found: C, 50.94; H, 5.41; N, 5.57.

The aqueous layer was concentrated to a white solid. A solution of the solid in CH$_2$Cl$_2$ with a few drops of methanol was added dropwise to rapidly stirring ethyl ether from which a white solid precipitated. The precipitate was collected and dried to give an additional quantity of N-[2-(4-morpholinyl)ethyl]-N-[[4-(phenylthio)-phenyl]sulfonyl]-D-alanine, monohydrochloride, (1.41 g, 34% yield) as a colorless solid.

EXAMPLE 3f

2R-[[[4-phenylthio)phenyl]sulfonyl][2-(4-morpholinyl)ethyl]amino]-N-[(tetrahydro-2H-pyran-2-yl)oxy]propanamide

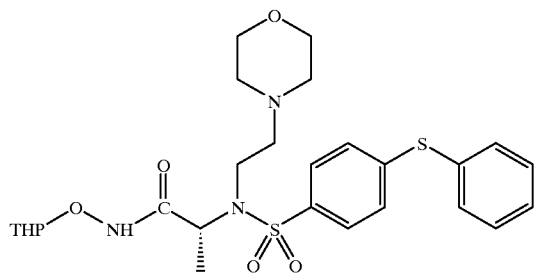

Ethyl-3-(3-dimethylamino)propyl carbonate hydrochloride (2.04 g, 10.6 mmol) was added to a room temperature solution of N-[2-(4-morpholinyl)ethyl]-N-[[4-(phenylthio)phenyl]sulfonyl]-D-alanine, monohydrochloride, from Example 3e (3.77 g, 7.74 mmol), 4-methylmorpholine (3.34 mL, 30.3 mmol), and N-hydroxybenzotriazole (1.23 g, 9.10 mmol) in dry DMF. After stirring for 10 minutes, O-tetrahydro-2H-pyran-2-yl-hydroxylamine (1.33 g, 11.4 mmol) was added and the solution was stirred at room temperature overnight. The reaction was concentrated and partitioned between water and ethyl acetate. The combined ethyl acetate layers were washed with water and brine, dried with MgSO$_4$, and concentrated to a white solid (4.80 g). Chromatographic purification (30% acetone in hexane) N-[2-(4-morpholinyl)ethyl]-N-[[4-(phenylthio)phenyl]sulfonyl]-D-alanine, tetrahydro-2H-pyran-2-yl ester, (3.51 g, 82% yield) as a white solid. The proton NMR was consistent with N-[2-(4-morpholinyl)ethyl]-N-[[4-(phenylthio)-phenyl]sulfonyl]-D-alanine, tetrahydro-2H-pyran-2-yl ester: anal. calc'd for C$_{26}$H$_{35}$N$_3$O$_6$S$_2$: C, 56.81; H, 6.42; N, 7.64. Found: C, 56.74; H, 6.66; N, 7.98.

EXAMPLE 3g

N-hydroxy-2R-[[2-(4-morpholinyl)ethyl][[4-(phenylthio)phenyl]sulfonyl]amino]propanamide

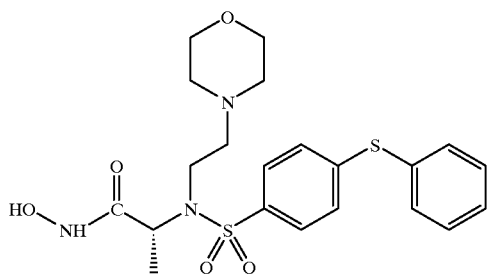

Dry HCl gas was bubbled into a zero degrees C. solution of N-[2-(4-morpholinyl)ethyl]-N-[[4-(phenylthio)-phenyl]sulfonyl]-D-alanine, tetrahydro-2H-pyran-2-yl ester from Example 3f (2.05 g, 3.73 mmol) in ethanol (40 mL) for 15 minutes. The solution was warmed to room temperature and stirred for 1 hour. The solution was concentrated and diethyl ether was added. Concentration again afforded a white solid (1.44 g). To the solid was added a saturated sodium bicarbonate solution and the mixture was extracted with methylene chloride. The combined organic layers were washed with water and brine, dried with MgSO$_4$, and concentrated. The residue was purified by flash chromatography (5% methanol in chloroform) to give N-hydroxy-2R-[[2-(4-morpholinyl)ethyl][[4-(phenylthio)-phenyl]sulfonyl]amino] propanamide (0.65 g, 37%) as a white solid. The proton NMR was consistent with N-hydroxy-2R-[2-(4-morpholinyl)ethyl][[4-(phenylthio)phenyl]sulfonyl]-amino] propanamide: MS MH+ calc'd for C$_{21}$H$_{27}$N$_3$O$_5$S$_2$: 466, found: 466; anal. calc'd for C21H27N3O5S2.0.1H2O: C, 53.97; H, 5.87; N, 8.99. Found; C, 53.73; H, 5.72; N, 8.87.

EXAMPLE 4a

N-[[4-[(4-methylphenyl)thio]phenyl]sulfonyl]-D-alanine

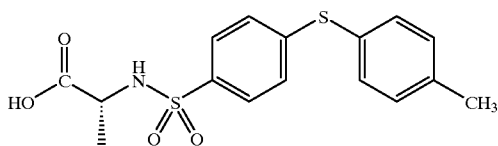

To N-[(4-fluorophenyl)sulfonyl]-D-alanine from Example 3a (10 g, 40.44 mmol) in DMAC was added p-thiocresol (15.07 g, 121.3 mmol) and powdered Cs$_2$CO$_3$ (54.04 g, 16.58 mmol). The mixture was heated to 100° C. for 15 hours. Then the mixture was concentrated and poured into water (400 mL). The aqueous layer was washed with ether (2×250 mL) before it was acidified with concentrated HCl to pH=2. The aqueous layer was then extracted with CH$_2$Cl$_2$ (2×200 mL) and the combined organic layers were dried over MgSO$_4$ and concentrated to give a white solid in quantitative yield. The proton NMR and MIR were consistent N-[[4-[(4-methylphenyl)thio]phenyl]sulfonyl]-D-alanine. HR mass calculated for C$_{16}$H$_{17}$NO$_4$S$_2$: 351.0599. Found: 351.0603.

EXAMPLE 4b

N-[[4-[(4-methylphenyl)thio]phenyl]sulfonyl]-D-alanine, methyl ester

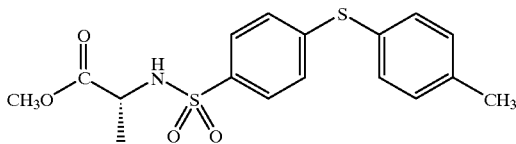

To N-[[4-[(4-methylphenyl)thio]phenyl)-sulfonyl]-D-alanine from Example 4a (14.89 g, 42.36 mmol) in methanol at zero degrees C. was added SOCl$_2$ (9.27 ml, 127.08 mmol) dropwise via addition funnel. After the addition was complete, the reaction was refluxed for 5 hours. Then the reaction solution was concentrated and chromatographic purification of the residue (20/80 ethyl acetate/hexane) afforded light a yellow oil which solidified (14.2 g, 91.6%). The proton NMR and IR were consistent with N-[[4-[(4-methylphenyl)thio]phenyl]sulfonyl]-D-alanine, methyl ester. Anal. calc'd for C$_{17}$H$_{19}$NO$_4$S$_2$: C, 55.87; H, 5.24; N, 3.83; S, 17.55. Found: C, 55.82; H, 5.48; N, 3.81; S, 17.55.

EXAMPLE 4c

N-[2-(4-morpholinyl)ethyl]-N-[[4-[(4-methylphenyl)thio]phenyl]sulfonyl]-D-alanine, methyl ester

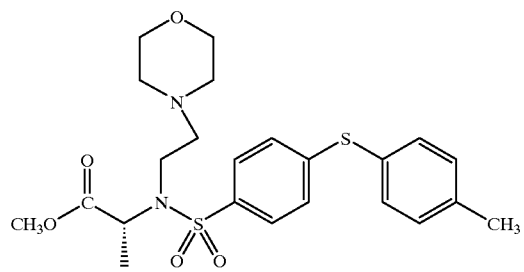

A mixture of N-[[4-[(4-methylphenyl)thio]phenyl] sulfonyl]-D-alanine, methyl ester from Example 4b (6.4 g, 17.5 mmol), 4-(2-chloroethyl)morpholine hydrochloride (9.77 g, 52.5 mmol), and potassium carbonate (10 g, 72.4 mmol) in dry DMF (60 mL) was heated to 70° C. for 16 hours. After cooling to room temperature, mixture was poured into water and extracted with ethyl acetate. The combined ethyl acetate layers were washed with water and brine, dried over MgSO$_4$, and concentrated to afford an oil which was purified by chromatography (40/100 acetone/hexane) to give N-[2-(4-morpholinyl)ethyl]-N-[[4-[(4-methylphenyl)thio]phenyl]sulfonyl]-D-alanine, methyl ester, (6.86 g, 81.86%) as an oil. The proton NMR was consistent with N-[2-(4-morpholinyl)ethyl]-N-[[4-[(4-methylphenyl)thio]phenyl]sulfonyl]-D-alanine, methyl ester. HR mass calculated for C$_{23}$H$_{30}$N$_2$O$_5$S$_2$: 478.1597.Found: 478.1596.

EXAMPLE 4d

N-[2-(4-morpholinyl)ethyl]-N-[[4-[(4-methylphenyl)thio]phenyl]sulfonyl]-D-alanine, monohydrochloride

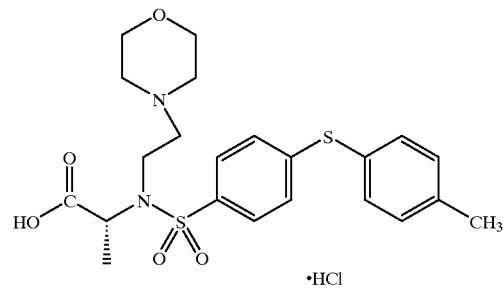

N-[2-(4-morpholinyl)ethyl]-N-[[4-[(4-methylphenyl)thio]phenyl]sulfonyl]-D-alanine, methyl ester from Example 4c (5.13 g, 10.7 mmol) in 6 N HCl (120 mL) was refluxed overnight. The reaction mixture was concentrated under high vacuum to afford white solid (4.48 g, 83.4% yield). The proton NMR was consistent with N-[2-(4-morpholinyl)ethyl]-N-[[4-[(4-methylphenyl)thio]-phenyl] sulfonyl]-D-alanine, monohydrochloride. Anal. calcd for C$_{22}$H$_{29}$N$_2$O$_5$S$_2$Cl.0.2H$_2$O: C, 52.36; H, 5.87; N, 5.55; S,12.71. Found: C, 51.99; H, 5.68; N, 5.37; S,13.05.

EXAMPLE 4e

2R-[[[4-[(4-methylphenyl)thio]phenyl]sulfonyl][2-(4-morpholinyl)]amino]-N-(tetrahydro-2H-pyran-2yl)oxy]propanamide

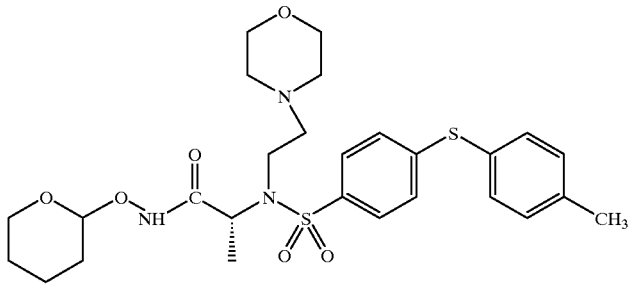

To the solution of N-[2-(4-morpholinyl)ethyl]-N-[[4-[(4-methylphenyl)thio]phenyl]sulfonyl]-D-alanine, monohydrochloride from Example 4d (3.61 g, 7.20 mmol) in dry DMF was added EDC (2.57 g, 13.4 mmol), 4-methylmorpholine (2.96 mL, 26.96 mmol), and N-hydroxybenzotriazole (1.81 g, 13.4 mmol) at zero degrees C. After stirring for 45 minutes at zero degrees C., O-tetrahydro-2H-pyran-2-yl-hydroxylamine (1.88 g, 16.0 mmol) was added and the solution was left stirring at room temperature overnight. The reaction was concentrated and partitioned between water and ethyl acetate. The combined ethyl acetate layers were washed with water and brine, dried with $MgSO_4$, and concentrated to a white solid (2.4 g). Chromatographic purification (40% acetone in hexane) afforded N-[2-(4-morpholinyl)ethyl]-N-[[4-[(4-methylphenyl)thio]phenyl]sulfonyl]-D-alanine, tetrahydro-2H-pyran-2-yl ester, (1.43 g, 34.6% yield) as a white solid. The proton NMR and MIR were consistent for N-[2-(4-morpholinyl)ethyl]-N-[[4-[(4-methylphenyl)thio]phenyl]sulfonyl]-D-alanine, tetrahydro-2H-pyran-2-yl ester. Anal. calc'd for $C_{27}H_{37}N_3O_6S_2$: C, 57.53; H, 6.62; N, 7.45; S, 11.38. Found: C, 57.43; H, 6.80; N, 7.34; S,11.34.

EXAMPLE 4f

N-hydroxy-2R-[[2-(4-morpholinyl)ethyl]][4-[(4-methylphenyl)thio]phenyl]sulfonyl]amino]-propanamide, monohydrochloride

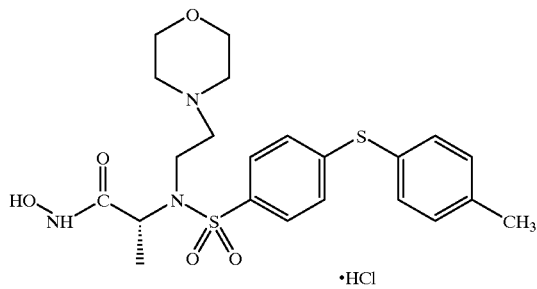

Dry HCl gas was bubbled into a zero degrees C. solution of the N-[2-(4-morpholinyl)ethyl]-N-[[4-[(4-methylphenyl)thio]phenyl]sulfonyl]-D-alanine, tetrahydro-2H-pyran-2-yl ester, from Example 4e (0.9 g, 1.59 mmol) in absolute ethanol (7 mL) for 15 minutes. The solution was concentrated to afford white solid. To the solid was added a saturated sodium bicarbonate solution and the mixture was extracted with methylene chloride. The combined organic layers were washed with water and brine, dried with $MgSO_4$, and concentrated. The residue was purified by flash chromatography (5/50/50 of methanol/ethyl acetate/hexane) to give white crystalline solid (0.7 g) as the free base of the title compound. This white crystalline free base compound, N-hydroxy-2R-[[2-(4-morpholinyl)ethyl][[4-[(4-methylphenyl)thio]phenyl]sulfonyl]amino]propanamide, was dissolved in acetonitrile (30 ml), and 12N HCl (0.24 ml, 2.9 mmol) was added to the solution. After 20 minutes stirring at room temperature, the reaction mixture was concentrated and residue was triturated with ether three times to afford N-hydroxy-2R-[[2-(4-morpholinyl)ethyl][[4-[(4-methylphenyl)thio]phenyl]sulfonyl]amino]propanamide, monohydrochloride (0.47 g, 57.3%) as a colorless powder. The proton NMR and MIR were consistent for the title compound. Anal. calc'd for $C_{22}H_{30}N_3O_5S_2Cl.0.5H_2O$: C, 50.32; H, 5.95; N, 8.00; S, 12.21. Found: C, 50.18; H, 5.79; N, 7.91; S, 12.37.

EXAMPLE 5a

N-[(4-flourophenyl)sulphonyl]glycine, 1,1-dimethylethyl ester

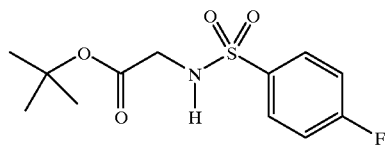

Tert-butyl glycine hydrochloride (20 mmol, 3.36 g) was suspended in acetonitrile (60 mL) in a room temperature water bath. Triethylamine (40 mmol, 6 mL) and dimethylaminopyridine (65 mg) were added, followed by 4-fluorobenzenesulphonyl chloride (20 mmol, 3.88 g). The mixture was stirred 4 hours, then diluted with water (80 mL) and extracted with ethyl acetate (400 mL, then 100 mL). The combined organic phases were dried over magnesium sulphate, filtered, and concentrated. The residue was re-diluted with ethyl acetate:methanol (9:1, 250 mL) and filtered through a silica plug, then concentrated to afford N-[(4-flouro-phenyl)sulphonyl]glycine, 1,1-dimethylethyl ester as a white solid (5.13 g, 89%). The structure was confirmed spectroscopically. DSC (10° C./min): 113.3–117.2° C.; 176.7–180.3° C.; elemental anal. calc'd for $C_{12}H_{16}NO_4SF$: C, 49.82; H, 5.54; N, 4.84. Found: C, 49.53; H, 5.47; N, 4.70.

EXAMPLE 5b

N-[[4-(cyclohexylthio)phenyl]sulfonyl]glycine, 1,1-dimethylethyl ester

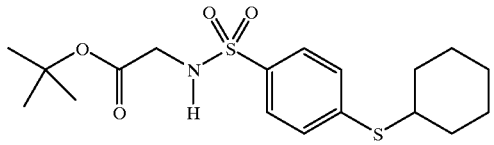

The N-[(4-flourophenyl)sulphonyl]glycine, 1,1-dimethylethyl ester from Example 5a (4.5 mmol, 1.30 g) was combined with dried 325 mesh $K_2CO_3$ (5.0 mmol, 0.69 g) and N,N-dimethylacetamide (4.5 mL). Cyclohexyl mercaptan (5 mmol, 0.61 mL) was added, and the mixture was stirred under argon at 60° C. for 40 hours. Water (50 mL) was added, and the mixture was extracted with ethyl acetate (125 mL). The organic phase was dried using magnesium sulphate, filtered through silica, and concentrated. The N-[[4-(cyclohexyl-thio)phenyl]sulfonyl]glycine, 1,1-dimethylethyl ester, a white solid (528 mg), was obtained following chromatography eluting with hexane:ethyl acetate (4:1). NMR indicated the presence of about 20% starting material after chromatography, but the mixture was used as is in the next step. The structure was confirmed spectroscopically.

EXAMPLE 5c

N-[[4-(cyclohexylthio)phenyl]phenyl]sulphonyl]-N-[2-(4-morpholinyl)ethyl]glycine, 1,1-dimethylethyl ester

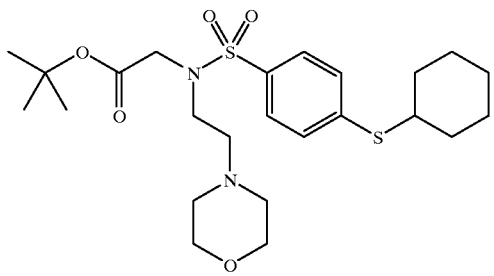

The N-[[4-(cyclohexylthio)phenyl]sulfonyl]glycine, 1,1-dimethylethyl ester, from Example 5b (3.34 mmol, 1.145 g), dried 325 mesh $K_2CO_3$ (13.4 mmol, 1.84 g), N-(chloroethyl) morpholine (10 mmol, 1.86 g), and N,N-dimethyacetamide (13 mL) were combined and heated at 60° C. under an inert atmosphere for 16 hours, then an additional 4 hours at 80° C. Water (40 mL) was added, and the mixture was extracted with ethyl acetate (100 mL, then 50 mL). The combined organic phases were dried ($MgSO_4$), filtered through a silica plug, concentrated, and subjected to chromatography (ethyl acetate:toluene 1:1), to afford N-[[4-(cyclohexylthio)phenyl]phenyl]sulphonyl]-N-[2-(4-morpholinyl)ethyl]-glycine, 1,1-dimethylethyl ester (954 mg, 57%) as an oil. The structure was verified spectroscopically. MS MH+ calcd. for $C_{24}H_{38}N_2O_5S_2$: 499, found: 499. Elemental anal. calc'd for $C_{24}H_{38}N_2O_5S_2.0.25H_2O$: C, 57.29; H, 7.71; N, 5.57. Found: C, 57.32; H, 8.21; N, 5.27.

EXAMPLE 5d

N-[[4-(cyclohexylthio)phenyl]sulfonyl]-N-[2-(4-morpholinyl)ethyl]glycine

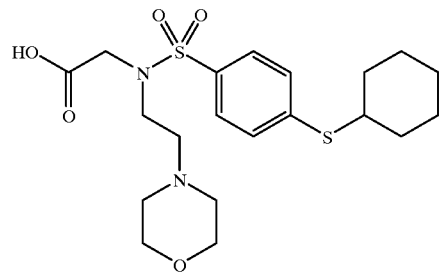

The N-[[4-(cyclohexylthio)phenyl]phenyl]sulphonyl]-N-[2-(4-morpholinyl)ethyl]glycine, 1,1-dimethylethyl ester from Example 5c (1.9 mmol, 954 mg) was diluted with water (1.5 mL) and concentrated HCl (1.5 mL), then brought to reflux. After 15 minutes, the reaction was concentrated, then azeotroped with toluene and dried in vacuo to afford N-[[4-(cyclohexylthio)phenyl]sulfonyl]-N-[2-(4-morpholinyl)ethyl]glycine as a white solid. The NMR was consistent with the proposed structure, and the compound was used without further purification.

EXAMPLE 5e

[[[4-(cyclohexylthio)phenyl]sulfonyl][2-(4-morpholinyl)ethyl]amino]-N-[tetetrahydro-2H-pyran-2-yl)oxy]acetamide

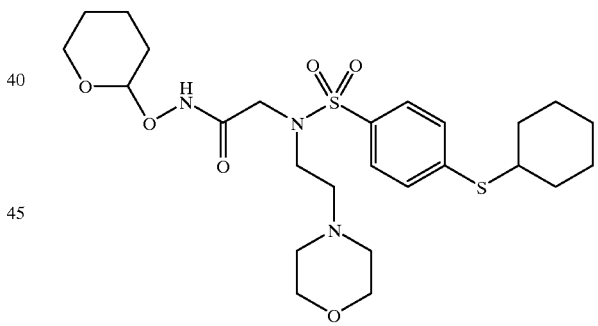

The N-[[4-(cyclohexylthio)phenyl]sulfonyl]-N-[2-(4-morpholinyl)ethyl]glycine from Example 5d (1.9 mmol), hydroxybenzotriazole (2.3 mmol, 0.308 g), O-tetrahydropyran hydroxylamine (5 mmol, 0.585 g), N,N-dimethylformamide (4 mL), and N-methyl morpholine (12 mmol, 1.32 mL) were combined, followed by the addition of EDC (2.3 mmol, 0.311 g). The mixture was stirred 40 hours at room temperature, then diluted with saturated sodium bicarbonate (20 mL). The suspension was extracted with ethyl acetate (100 mL) and washed with brine (20 mL). The organic phase was dried ($MgSO_4$), filtered, and concentrated. Chromatography (ethyl acetate) afforded [[[4-(cyclohexylthio)phenyl]sulfonyl][2-(4-morpholinyl)ethyl]amino]-N-[tetrahydro-2H-pyran-2-yl)oxy]acetamide as an oil (842 mg). The structure was confirmed spectroscopically.

EXAMPLE 5f

[[[4-(Cyclohexylthio)phenyl]sulphonyl][2-(4-morpholinyl)ethyl]amino]-N-hydroxyacetamide

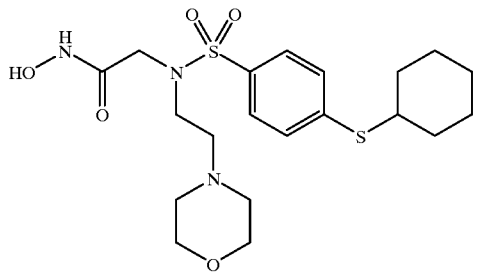

The [[[4-(cyclohexylthio)phenyl]sulfonyl][2-(4-morpholinyl)ethyl]amino]-N-[tetrahydro-2H-pyran-2-yl)oxy]acetamide from Example 5e (842 mg) was dissolved in cold (zero degrees C.) methanol (50 mL) and anhydrous HCl was bubbled through the solution for 5 minutes. The solution was concentrated, then azeotroped with toluene (3 mL). The residue was taken up in methanol (2 mL) and added to dry ether (250 mL). Concentration afforded a white foam. Further purification was effected by dissolving the compound in 3% methanol:chloroform, adding triethylamine (0.6 mL) and performing flash chromatography (3% methanol:chloroform). Upon concentration, [[[4-(cyclohexylthio)phenyl]sulphonyl][2-(4-morpholinyl)ethyl]amino]-N-hydroxyacetamide (441 mg) was obtained as a white solid. The structure was confirmed spectroscopically. MS MH+ calc'd for $C_{20}H_{31}N_3O_5S_2$: 458, found 458. DSC (10° C./min): 141.4–145.3° C. Elemental anal. calc'd for $C_{20}H_{31}N_3O_5S_2$: C, 52.49; H, 6.83; N, 9.18. Found: C, 52.34; H, 6.59; N, 9.67.

EXAMPLE 6a

N-[[4-(phenylthio)phenyl]sulfonyl]glycine, 1,1-dimethylethyl ester

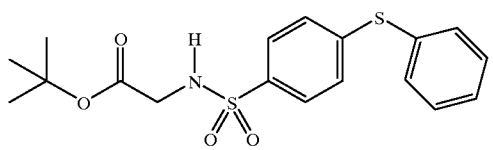

To a solution of 12.0 g (41.6 mmol) of N-[(4-fluorophenyl)sulfonyl]glycine, 1,1-dimethylethyl ester from Example 5a and 12.8 mL (125 mmol) of thiophenol in 80 mL of anhydrous dimethylformamide, previously degassed by passing nitrogen through the solution, was added 17.3 g (125 mmol) of powdered potassium carbonate. The mixture was vigorously stirred and warmed to 70° C. and maintained there for 13 hours, cooled and ethyl acetate and water added. The organic layer was separated, washed four times with brine, dried over anhydrous sodium sulfate, filtered and concentrated to afford crude product. This was triturated with diethyl ether and hexanes, and the solids filtered and air dried to yield 15.3 g of title compound N-[[4-(phenylthio)phenyl]sulfonyl]glycine, 1,1-dimethylethyl ester, m/e=386 (M+H).

EXAMPLE 6b

N-[[4-(phenylthio)phenyl]sulfonyl]-N-[2-(4-morpholinyl)ethyl]glycine, 1,1-dimethylethyl ester

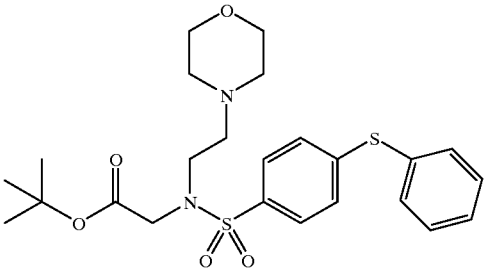

To a solution of 10 g (26.3 mmol) of N-[[4-(phenylthio)phenyl]sulfonyl]glycine, 1,1-dimethylethyl ester from Example 6a in 50 mL of anhydrous dimethylformamide, was added 9.80 g (52.7 mmol) of 4-(2-chloroethyl)morpholine hydrochloride, followed by 10.9 g (79.0 mmol) of powdered potassium carbonate. The mixture was heated to 50° C. with vigorous stirring and maintained there for 20 hours. A sample was removed and analyzed by HPLC and shown to contain starting material, whereupon 4.90 g (26.3 mmol) of 4-(2-chloroethyl)morpholine hydrochloride, followed by 3.63 g (26.3 mmol) of powdered potassium carbonate was added and heating continued for an additional 4 hours at 70° C. The solution was cooled, ethyl acetate and water added, the organic layer separated and washed 4 times with brine, dried with sodium sulfate, filtered and concentrated to afford crude product. This was chromatographed on silica gel using 0–5% methanol/ethyl acetate to yield 12.9 g of pure N-[[4-(phenylthio)phenyl]sulfonyl]-N-[2-(4-morpholinyl)ethyl]glycine, 1,1-dimethylethyl ester, m/e=490 (M+H).

EXAMPLE 6c

-[[4-(phenylthio)phenyl]sulfonyl]-N-[2-(4-morpholinyl)ethyl]glycine, hydrochloride salt

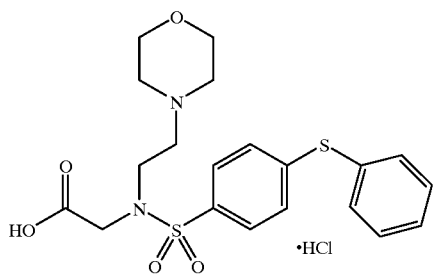

To a mixture of 12.8 g (25.9 mmol) of N-[[4-(phenylthio)phenyl]sulfonyl]-N-[2-(4-morpholinyl)ethyl]-glycine, 1,1-dimethylethyl ester from Example 6b in 100 mL of water, was added 100 mL of 12N hydrochloric acid. The mixture was heated to reflux and maintained there for 15 minutes, cooled to room temperature and concentrated to afford a clear oil. Acetone was added and remove under reduced pressure twice to yield 11.3 g of title compound N-[[4-(phenylthio)phenyl]sulfonyl]-N-[2-(4-morpholinyl)ethyl]-glycine, hydrochloride salt, m/e=437 (M+H), as a glassy solid.

EXAMPLE 6d

2-[[4-[(phenylthio)phenyl]sulfonyl]-[2-(4-morpholinyl)ethyl]amino]-N-[(tetrahydro-2H-pyran-2-yl)oxy]acetamide

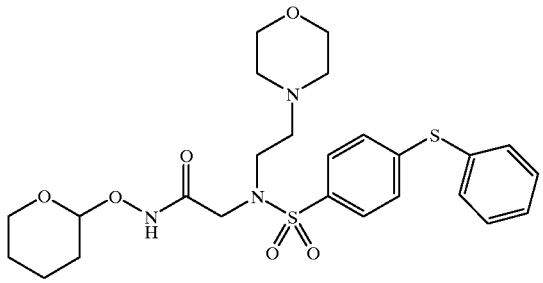

To a solution of 11.3 g (23.9 mmol) of N-[[4-(phenylthio)phenyl]sulfonyl]-N-[2-(4-morpholinyl)ethyl]-glycine, hydrochloride salt, from Example 6c in 80 mL of anhydrous dimethylformamide, was added 3.87 g (28.7 mmol) of N-hydroxybenzotriazole, 15.7 mL (143 mmol) of N-methylmorpholine, 9.7 g (74 mmol) of O-tetrahydro-2H-pyran-2-yl-hydroxylamine and then 6.4 g (33.5 mmol) of N-(3-dimethylaminopropyl)-N'-ethylcarbodiimide hydrochloride. After stirring at room temperature for 14 hours, ethyl acetate and water were added and the organic layer separated, washed three times with brine, dried with sodium sulfate, filtered and concentrated to afford crude product. This was chromatographed on silica gel using 0–5% methanol/ethyl acetate to yield 10.37 g of pure 2-[[4-[(phenylthio)phenyl]sulfonyl]-[2-(4-morpholinyl)ethyl]amino]-N-[(tetrahydro-2H-pyran-2-yl)oxy]acetamide, m/e= 542 (M+Li).

EXAMPLE 6e

2-[[[4-(phenylthio)phenyl]sulphonyl][2-(4-morpholinyl)ethyl]amino]-N-hydroxyacetamide, hydrochloride

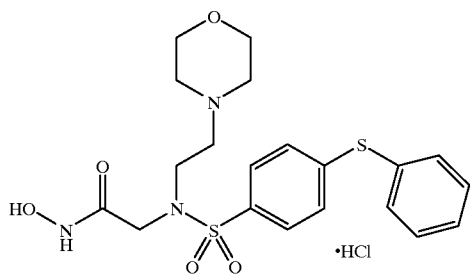

To a solution of 1.20 g of 2-[[4-[(phenylthio)-phenyl]sulfonyl]-[2-(4-morpholinyl)ethyl]amino]-N-[(tetra-hydro-2H-pyran-2-yl)oxy]acetamide from Example 6d, suspended in 15 mL of anhydrous ethanol at zero degrees C., was bubbled in anhydrous hydrochloric acid for approximately 2 minutes and until all the solids dissolved. After 5 minutes, the solution was purged with nitrogen and concentrated to afford crude product. This was dissolved in 15 mL of warm ethanol and cooled, whereupon a solid precipitated. Diethyl ether was added and the solid collected to yield 762 mg of pure 2-[[[4-(Phenylthio)phenyl]sulphonyl][2-(4-morpholinyl)ethyl]amino]-N-hydroxyacetamide, hydrochloride, m/e=452 (M+H).

EXAMPLE 7a

N-[(4-fluorophenyl)sulfonyl]-D-valine, ethyl ester

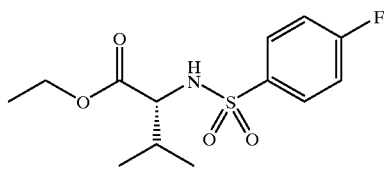

To a solution of 15.0 g (54 mmol) of N-[(4-fluorophenyl)sulfonyl]-D-valine from Example 1a in 55 mL of anhydrous ethanol cooled in an ice bath, was slowly added 5.0 mL (8.1 g, 68 mmol) of thionyl chloride over 5 minutes. The reaction mixture was then stirred at room temperature for 28 hours, the solvents removed under reduced pressure and the residue dissolved in ethyl acetate. This was then washed with saturated sodium bicarbonate, 5% potassium hydrogen sulfate and brine, dried over sodium sulfate, filtered and concentrated to afford crude product, which was chromatographed on silica gel using 10–20% ethyl acetate/hexane to yield 12.8 g of pure N-[(4-fluorophenyl)sulfonyl]-D-valine ethyl ester, m/e=304 (M+H).

EXAMPLE 7b

N-[[4-(phenylthio)phenyl]sulfonyl])-D-valine, ethyl ester

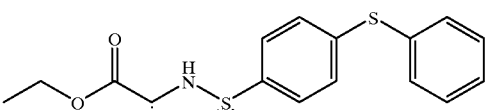

To a solution of 7.76 g (25.6 mmol) of N-[(4-fluorophenyl)sulfonyl]-D-valine ethyl ester from Example 7a in 50 mL of anhydrous dimethylformamide was added 7.8 mL (77 mmol) of thiophenol. After purging with nitrogen for 5 minutes, 10.6 g (77 mmol) of powdered potassium carbonate was added and the reaction heated to 70° C. for 21 hours. The solution was cooled, water and ethyl acetate added and separated. The ethyl acetate layer was washed with saturated sodium bicarbonate, three times with brine, dried with sodium sulfate, filtered and concentrated to afford crude product. This was chromatographed on silica gel using 20% ethyl acetate/hexane to yield 4.2 g of N-[[4-(phenylthio)phenyl]sulfonyl]-D-valine ethyl ester, m/e=400 (M+Li).

EXAMPLE 7c

N-[[(4-phenylthio)phenyl]sulfonyl]-N-[2-(4-morpholinyl)ethyl]-D-valine, ethyl ester

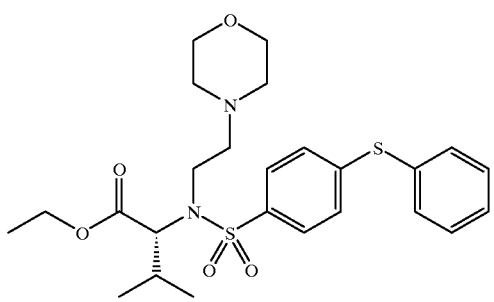

To a solution of 4.35 g (11.0 mmol) of N-[[4-(phenylthio)phenyl]sulfonyl]-D-valine ethyl ester from Example 7b in 22 mL of anhydrous dimethylformamide, was added 3.08 g (16.6 mmol) of 4-(2-chloroethyl)morpholine hydrochloride followed by 4.58 g (33.1 mmol) of powdered potassium carbonate. The reaction was then heated at 50° C. for 17 hours, cooled and water and ethyl acetate added. The ethyl acetate layer was separated, washed three times with brine, dried with sodium sulfate, filtered and concentrated to afford 6.2 g of title compound N-[[(4-phenylthio)phenyl]sulfonyl]-N-[2-(4-morpholinyl)ethyl]-D-valine, ethyl esler, m/e=507 (M+H), suitable for use in the next step.

EXAMPLE 7d

N-[[(4-phenylthio)phenyl]sulfonyl]-N-[2-(4-morpholinyl)ethyl]-D-valine, hydrochloride salt

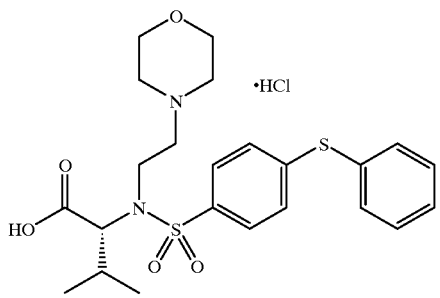

To a mixture of 6.2 g (12.2 mmol) of N-[[(4-phenylthio)phenyl]sulfonyl]-N-[2-(4-morpholinyl)ethyl]D-valine, ethyl ester from Example 7c in 91 mL of water was added 91 mL of 12N hydrochloric acid and the reaction heated to reflux for 21 hours. The solvents were removed under reduced pressure to afford 6.29 g of N-[[(4-phenylthio)phenyl]sulfonyl]-N-[2-(4-morpholinyl)ethyl]-D-valine, hydrochloride salt, m/e=479 (M+H)

EXAMPLE 7e 3-methyl-2R-[[[(4-phenylthio)phenyl]sulfonyl]-[2-(4-morpholinyl)ethyl]amino]-N-[(tetrahydro-2H-pyran-2-yl)oxy]butanamide

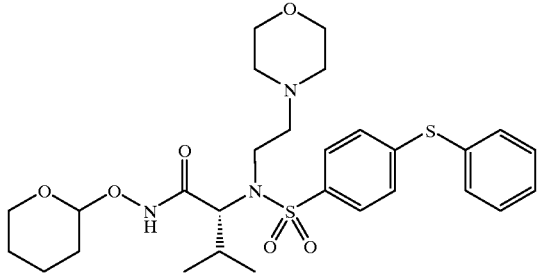

To a solution of N-[[(4-phenylthio)phenyl]sulfonyl]-N-[2-(4-morpholinyl)ethyl]-D-valine, hydrochloride salt, from Example 7d (6.2 g; 12 mmol) in 45 mL of anhydrous dimethylformamide, was added N-hydroxybenzotriazole (1.94 g; 14.4 mmol), N-methylmorpholine (7.9 mL; 72 mmol), O-tetrahydro-2H-pyran-2-yl-hydroxylamine (4.37 g; 37.3 mmol) and then N-(3-dimethylaminopropyl)-N'-ethylcarbodiimide hydrochloride (3.23 g; 16.6 mmol). After stirring at room temperature for 21 hours, ethyl acetate and water were added and the organic layer separated, washed three times with brine, dried with sodium sulfate, filtered and concentrated to afford crude product. This was chromatographed on silica gel using 50–100% ethyl acetate/hexane followed by 5% methanol/ethyl acetate to yield 3-methyl-2R-[[(4-phenylthio)phenyl]sulfonyl]-[2-(4-morpholinyl)ethyl]amino]-N-[tetrahydro-2H-pyran-2-yl)oxy]butanamide (4.9 g), m/e 578(M+H).

EXAMPLE 7f

N-hydroxy-3-methyl-2R-[[(4-phenylthio)phenyl]-sulfonyl]-[2-(4-morpholinyl)ethyl]amino]-butanamide, monohydrochloride

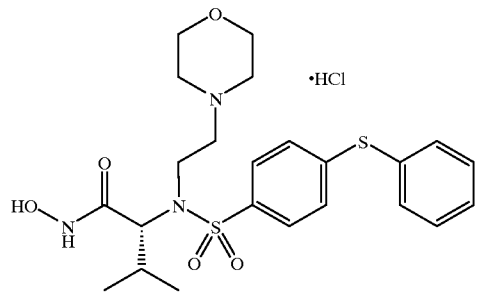

A solution of 3-methyl-2R-[[(4-phenylthio)phenyl]sulfonyl]-[2-(4-morpholinyl)ethyl]amino]-N-[tetrahydro-2H-pyran-2-yl)oxy]butanamide from Example 7e (4.9 g) in 40 mL of anhydrous methanol cooled in an ice bath was bubbled with anhydrous gaseous hydrochloric acid for 15 minutes. The solvents were removed under reduced pressure and the solids triturated with diethyl ether to afford pure N-hydroxy-3-methyl-2R-[[(4-phenylthio)phenyl]sulfonyl]-[2-(4-morpholinyl)ethyl]amino]butanamide, monohydrochloride, (3.75 g) m/e=494 (M+H).

EXAMPLE 8a

N-[[(4-phenylthio)phenyl]sulfonyl]-N-[2-(1-piperidinyl)ethyl]-D-valine, ethyl ester

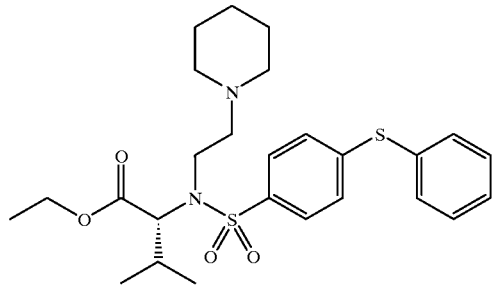

To a solution of N-[[4-(phenylthio)phenyl]sulfonyl]-D-valine ethyl ester from Example 7b (3.00 g; 7.62 mmol) in 17 mL of anhydrous dimethylformamide, was added 1-(2-chloroethyl)piperidine hydrochloride (2.10 g; 11.4 mmol) followed by powdered potassium carbonate(3.16 g; 22.9 mmol). The reaction was then heated at 50° C. for 15 hours, cooled, and water and ethyl acetate added. The ethyl acetate layer was separated, washed three times with brine, dried with sodium sulfate, filtered and concentrated to afford crude product. This was chromatographed on silica gel using 5% methanol/ethyl acetate to yield N-[[(4-phenylthio)phenyl]-sulfonyl]-N-[2-(1-piperidinyl)ethyl]-D-valine, ethyl ester, (3.50 g) m/e=505 (M+H).

EXAMPLE 8b

N-[[(4-phenylthio)phenyl]sulfonyl]-N-[2-(1-piperidinyl)ethyl]-D-valine, hydrochloride salt

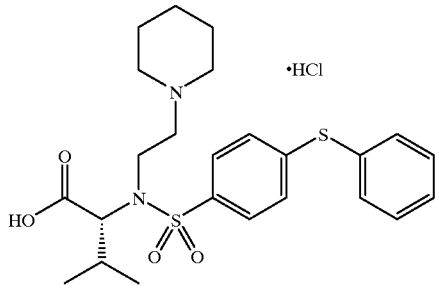

To a mixture of 3.5 g of N-[[(4-phenylthio)phenyl]sulfonyl]-N-[2-(1-piperidinyl)ethyl]-D-valine, ethyl ester from Example 8a in 51 mL of water was added 51 mL of 12N hydrochloric acid and the reaction heated to reflux for 20 hours. The solvents were removed under reduced pressure to afford N-[[(4-phenylthio)phenyl]sulfonyl]-N-[2-(1-piperidinyl)ethyl]-D-valine, hydrochloride salt (3.5 g), suitable for use in the next step.

EXAMPLE 8c 3-methyl-2R-[[(4-phenylthio)phenyl]sulfonyl]-[2-(1-piperidinyl)ethyl]amino]-N-[(tetrahydro-2H-pyran-2-yl)oxy]butanamide

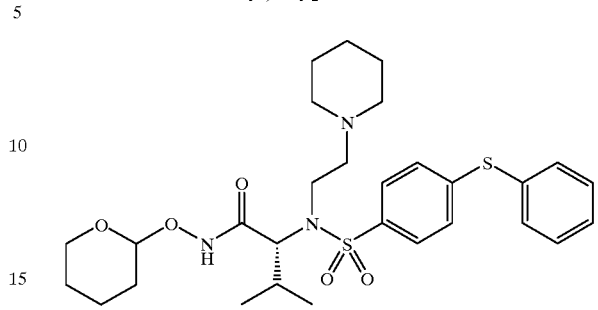

To a solution of N-[[(4-phenylthio)phenyl]sulfonyl]-N-[2-(1-piperidinyl)ethyl]-D-valine, hydrochloride salt from Example 8b (3.5 g; 6.8 mmol) in 23 mL of anhydrous dimethylformamide, was added N-hydroxybenzotriazole (1.10 g; 8.2 mmol), N-methylmorpholine (4.5 mL; 40.9 mmol), O-tetrahydro-2H-pyran-2-yl-hydroxylamine (2.48 g; 21.1 mmol), and then N-(3-dimethylaminopropyl)-N'-ethylcarbodiimide hydrochloride (1.83 g; 9.54 mmol). After stirring at room temperature for 25 hours, ethyl acetate and water were added and the organic layer separated, washed three times with brine, dried with sodium sulfate, filtered and concentrated to afford crude product. This was chromatographed on silica gel using 0–100% tetrahydrofuran/ethyl acetate to yield pure 3-methyl-2R-[[(4-phenylthio)phenyl]sulfonyl]-[2-(1-piperidinyl)ethyl]amino]-N-[tetrahydro-2H-pyran-2-yl)oxy]butanamide (2.9 g), m/e=576 (M+H).

EXAMPLE 8d

N-hydroxy-3-methyl-2R-[[(4-phenylthio)phenyl]-sulfonyl]-[2-(1-piperidinyl)ethyl]amino]-butanamide, monohydrochloride

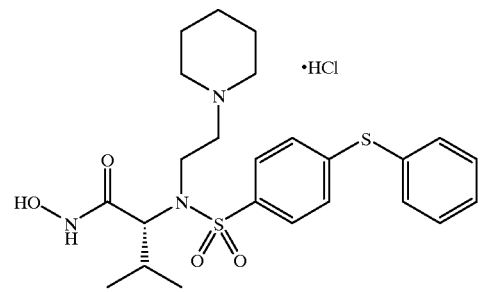

A solution of 3-methyl-2R-[[(4-phenylthio)phenyl]-sulfonyl]-[2-(1-piperidinyl)ethyl]amino]-N-[(tetrahydro-2H-pyran-2-yl)oxy]butanamide from Example 8c (2.98 g; 5.18 mmol), in 20 mL of anhydrous methanol cooled in an ice bath, was bubbled in anhydrous gaseous hydrogen chloride for 15 minutes. The solvents were removed under reduced pressure and the solids triturated with diethyl ether to afford N-hydroxy-3-methyl-2R-[[(4-phenylthio)phenyl]sulfonyl]-[2-(1-piperidinyl)ethyl]amino]butanamide, monohydrochloride (2.46 g), m/e=492 (M+H).

EXAMPLE 9

In Vitro Metalloprotease Inhibition

Several of the compounds prepared in the manner described in the previous Examples were assayed for activity by an in vitro assay. Following the procedures of Knight et al., FEBS Lett. 296(3):263 (1992). Briefly, 4-aminophenylmercuric acetate (APMA) or trypsin activated MMPs were incubated with various concentrations of the inhibitor compound at room temperature for 5 minutes.

More specifically, recombinant human MMP-13 and MMP-1 enzymes were prepared in laboratories of the assignee. MMP-13 was expressed in baculovirus as a proenzyme, and purified first over a heparin agarose column and then over a chelating zinc chloride column. The proenzyme was activated by APMA for use in the assay. MMP-1 expressed in transfected HT-1080 cells was provided by Dr. Howard Welgus of Washington University, St. Louis, Mo. The enzyme was also activated using APMA and was then purified over a hydroxamic acid column.

The enzyme substrate is a methoxycoumarin-containing polypeptide having the following sequence:

MCA-ProLeuGlyLeuDpaAlaArgNH$^2$, wherein MCA is methoxycoumarin and Dpa is 3-(2,4-dinitrophenyl)-L-2,3-diaminopropionyl alanine. This substrate is commercially available from Baychem as product M-1895.

The buffer used for assays contained 100 mM Tris-HCl, 100 mM NaCl, 10 mM $CaCl_2$ and 0.05 percent polyethyleneglycol (23) lauryl ether at a pH value of 7.5. Assays were carried out at room temperature, and dimethyl sulfoxide (DMSO) at a final concentration of 1 percent was used to dissolve inhibitor compound.

The assayed inhibitor compound in DMSO/buffer solution was compared to an equal amount of DMSO/buffer with no inhibitor as control using Microfluor™ White Plates (Dynatech). The inhibitor or control solution was maintained in the plate for 10 minutes and the substrate was added to provide a final concentration of 4 $\mu$M.

In the absence of inhibitor activity, a fluorogenic peptide was cleaved at the gly-leu peptide bond, separating the highly fluorogenic peptide from a 2,4-dinitrophenyl quencher, resulting in an increase of fluorescence intensity (excitation at 328 nm/emission at 415 nm). Inhibition was measured as a reduction in fluorescent intensity as a function of inhibitor concentration, using a Perkin Elmer L550 plate reader. The $IC_{50}$ values were calculated from those values. The results are set forth in the Inhibition Table below, reported in terms of $IC_{50}$.

INHIBITION TABLE ($IC_{50}$ values in nM)
MMP ENZYME INHIBITION PROFILE

| COMPOUND OF | MMP-13 $IC_{50}$ (nM) | MMP-1 $IC_{50}$ (nM) |
|---|---|---|
| Example 1g | 1.9 | 1,500 |
| Example 2e | 0.5 | 2,000 |
| Example 3g | 0.5 | 1,800 |
| Example 4f | 0.1 | >10,000 |
| Example 5f | 1.6 | >10,000 |
| Example 6e | 0.1 | 4,000 |
| Example 7f | 0.3 | 560 |
| Example 8d | 1 | 500 |

EXAMPLE 10

In Vivo Angiogenesis Assay

The study of angiogenesis depends on a reliable and reproducible model for the stimulation and inhibition of a neovascular response. The corneal micropocket assay provides such a model of angiogenesis in the cornea of a mouse. See, A Model of Angiogenesis in the Mouse Cornea; Kenyon, B M, et al., Investigative Ophthalmology & Visual Science, July 1996, Vol. 37, No. 8.

In this assay, uniformly sized Hydron™ pellets containing bFGF and sucralfate are prepared and surgically implanted into the stroma mouse cornea adjacent to the temporal limbus. The pellets are formed by making a suspension of 20 $\mu$L sterile saline containing 10 $\mu$g recombinant bFGF, 10 mg of sucralfate and 10 $\mu$L of 12 percent Hydron™ in ethanol. The slurry is then deposited on a 10×10 mm piece of sterile nylon mesh. After drying, the nylon fibers of the mesh are separated to release the pellets.

The corneal pocket is made by anesthetizing a 7 week old C57Bl/6 female mouse, then proptosing the eye with a jeweler's forceps. Using a dissecting microscope, a central, intrastromal linear keratotomy of approximately 0.6 mm in length is performed with a #15 surgical blade, parallel to the insertion of the lateral rectus muscle. Using a modified cataract knife, a lamellar micropocket is dissected toward the temporal limbus. The pocket is extended to within 1.0 mm of the temporal limbus. A single pellet is placed on the corneal surface at the base of the pocket with a jeweler's forceps. The pellet is then advanced to the temporal end of the pocket. Antibiotic ointment is then applied to the eye.

Mice are dosed on a daily basis for the duration of the assay. Dosing of the animals is based on bioavailability and overall potency of the compound. an exemplary dose is 50 mg/kg bid, po. Neovascularization of the corneal stroma begins at about day three and is permitted to continue under the influence of the assayed compound until day five. At day five, the degree of angiogenic inhibition is scored by viewing the neovascular progression with a slit lamp microscope.

The mice are anesthetized and the studied eye is once again proptosed. The maximum vessel length of neovascularization, extending from the limbal vascular plexus toward the pellet is measured. In addition, the contiguous circumferential zone of neovascularization is measured as clock hours, where 30 degrees of arc equals one clock hour. The area of angiogenesis is calculated as follows.

$$\text{area} = \frac{(0.4 \times \text{clock hours} \times 3.14 \times \text{vessel length (in mm)})}{2}$$

The studied mice are thereafter compared to control mice and the difference in the area of neovascularization is recorded. A contemplated compound typically exhibits about 25 to about 75 percent inhibition, whereas the vehicle control exhibits zero percent inhibition.

From the forgoing description, one skilled in the art can easily ascertain the essential characteristics of this invention, and without departing from the spirit and scope thereof, can make various changes and modifications of the invention to adapt it to various usages and conditions.

What is claimed is:

1. A compound or salt that corresponds in structure to Formula III

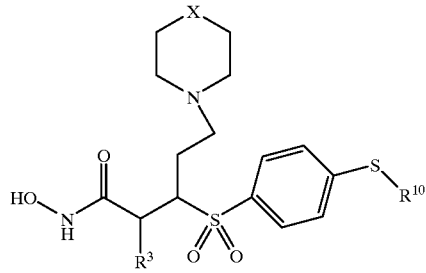

wherein
$R^3$ is selected from the group consisting of a hydrido, alkyl, cycloalkyl, cycloalkylalkyl, alkoxyalkyl, hydroxyalkyl, aryloxyalkyl, aralkoxyalkyl, aralkyl, aryl, heteroaryl, heteroaralkyl, heterocyclo, heterocycloalkyl, hydroxycarbonylalkyl, alkoxycarbonylalkyl, aralkoxycarbonylalkyl, hydroxycarbonyl, alkoxycarbonyl, perfluoroalkyl, trifluoromethyl, trifluoromethylalkyl, thiolalkyl, alkylthioalkyl, arylthioalkyl, aralkylthioalkyl, heteroaralkylthioalkyl, or a sulfoxide or sulfone of any of said thio substituents, aminocarbonyl, aminocarbonylalkyl and N-monosubstituted or N,N-disubstituted aminocarbonyl or aminocarbonylalkyl group wherein the substituents on the nitrogen are independently selected from among alkyl, aryl, aralkyl, heteroaralkyl, cycloalkyl and alkanoyl, or wherein the nitrogen and two substituents attached thereto form a 5- to 8-membered heterocyclo or heteroaryl ring, and
$R^{10}$ is a six-membered aryl, cycloalkyl or heteroaryl ring and X is O or $CH_2$.

2. The compound or salt according to claim 1 wherein $R^1$ is an aryl or heteroaryl group.

3. The compound or salt according to claim 1 wherein $R^3$ is an alkyl group.

4. The compound or salt according to claim 1 that corresponds in structure to Formula IIIA

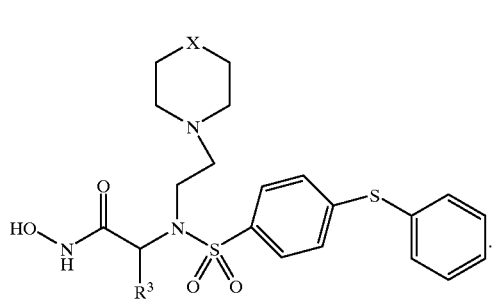

5. The compound or salt according to claim 1 that corresponds in stereoconfiguration to Formula V

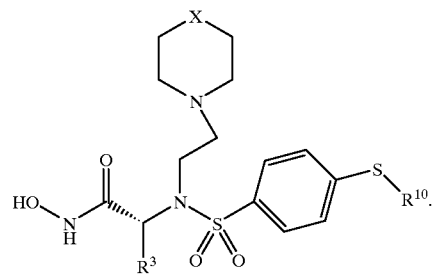

6. A compound or salt corresponding in structure to the formula

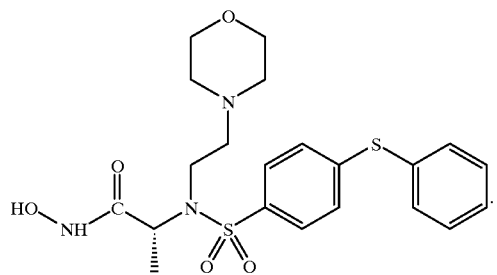

7. A compound or salt corresponding in structure to the formula

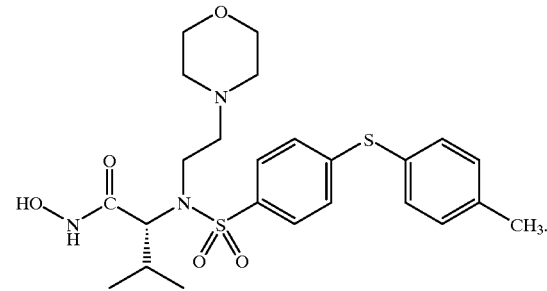

8. A compound or salt corresponding in structure to the formula

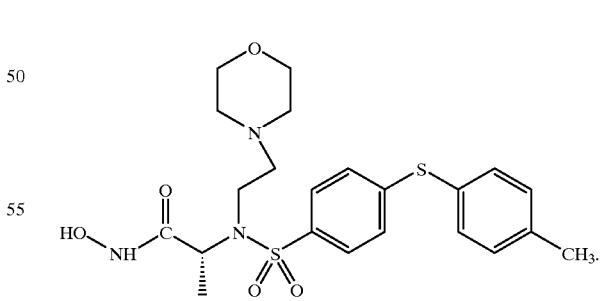

9. A compound or salt corresponding in structure to the formula

10. A compound or salt corresponding in structure to the formula

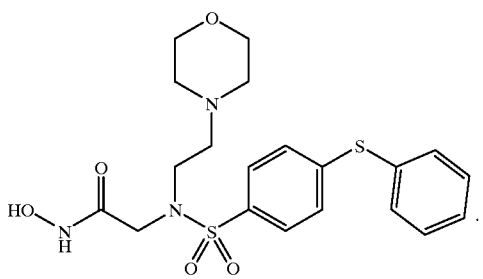

11. A compound or salt corresponding in structure to the formula

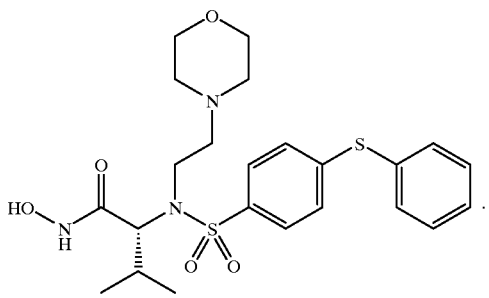

12. A compound or salt corresponding in structure to the formula

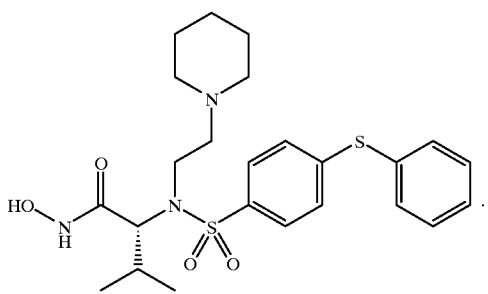

13. A compound or salt corresponding in structure to the formula

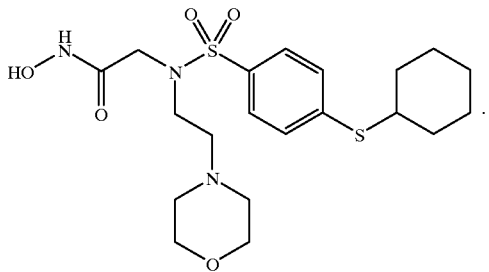

14. A process for treating a host mammal having a condition associated with pathological matrix metalloprotease activity that comprises administering a compound corresponding in structure to Formula III or salt thereof in an MMP enzyme-inhibiting effective amount to a mammalian host having such a condition:

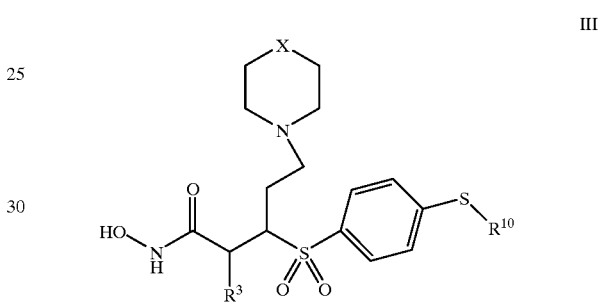

III wherein $R^3$ is selected from the group consisting of a hydrido, alkyl, cycloalkyl, cycloalkylalkyl, alkoxyalkyl, hydroxyalkyl, aryloxyalkyl, aralkoxyalkyl, aralkyl, aryl, heteroaryl, heteroaralkyl, heterocyclo, heterocycloalkyl, hydroxycarbonylalkyl, alkoxycarbonylalkyl, aralkoxycarbonylalkyl, hydroxycarbonyl, alkoxycarbonyl, perfluoroalkyl, trifluoromethyl, trifluoromethylalkyl, thiolalkyl, alkylthioalkyl, arylthioalkyl, aralkylthioalkyl, heteroaralkylthioalkyl, or a sulfoxide or sulfone of any said thio substituents, aminocarbonyl, aminocarbonylalkyl and N-monosubstituted or N,N-disubstituted aminocarbonyl or aminocarbonylalkyl group wherein the substituents on the nitrogen are independently selected from among alkyl, aryl, aralkyl, heteroaralkyl, cycloalkyl and alkanoyl, or wherein the nitrogen and two substituents attached thereto form a 5- to 8-membered heterocyclo or heteroaryl ring, and $R^{10}$ is a six-membered aryl, cycloalkyl or heteroaryl ring and X is O or $CH_2$.

15. The process according to claim 14 wherein $R^1$ is an aryl or heteroaryl group.

16. The process according to claim 14 wherein $R^3$ is an alkyl group.

17. The process according to claim 14 wherein said compound corresponds in structure to Formula IIIA

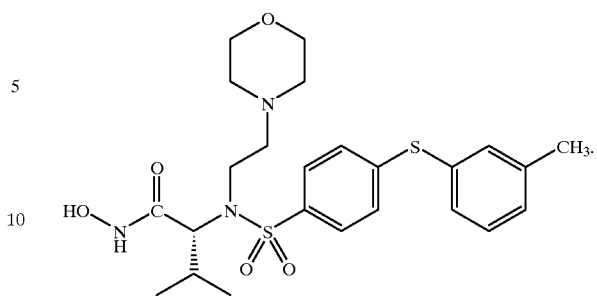

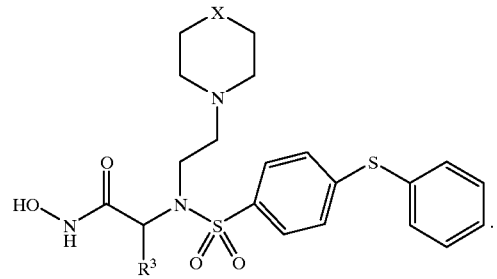
IIIA
18. The process according to claim 14 wherein said compound corresponds in structure to Formula V
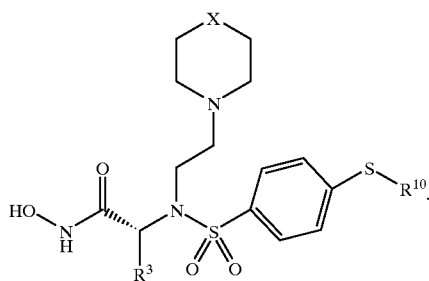
V
19. The process according to claim 14 that is repeated a plurality of times.
* * * * *